(12) United States Patent
Lipkens et al.

(10) Patent No.: US 9,745,569 B2
(45) Date of Patent: *Aug. 29, 2017

(54) SYSTEM FOR GENERATING HIGH CONCENTRATION FACTORS FOR LOW CELL DENSITY SUSPENSIONS

(71) Applicant: FloDesign Sonics, Inc., Wilbraham, MA (US)

(72) Inventors: Bart Lipkens, Hampden, MA (US); Jason Dionne, Simsbury, CT (US); Goutam Ghoshal, Springfield, MA (US)

(73) Assignee: FloDesign Sonics, Inc., Wilbraham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/417,181

(22) Filed: Jan. 26, 2017

(65) Prior Publication Data

US 2017/0137802 A1    May 18, 2017

Related U.S. Application Data

(63) Continuation-in-part of application No. 15/285,434, filed on Oct. 4, 2016, which is a continuation of (Continued)

(51) Int. Cl.
*C12M 1/12* (2006.01)
*C12N 13/00* (2006.01)
(Continued)

(52) U.S. Cl.
CPC ............ *C12N 13/00* (2013.01); *C12M 47/02* (2013.01); *G10K 15/043* (2013.01)

(58) Field of Classification Search
CPC ...... B01D 29/115; B01D 37/00; B01D 29/52; B01D 29/865; B01D 2201/0415;
(Continued)

(56) References Cited

U.S. PATENT DOCUMENTS

| 2,473,971 A | 6/1949 | Ross |
| 2,667,944 A | 2/1954 | Crites |

(Continued)

FOREIGN PATENT DOCUMENTS

| DE | 30 27 433 A1 | 2/1982 |
| DE | 32 18 488 A1 | 11/1983 |

(Continued)

OTHER PUBLICATIONS

Alvarez et al.; Shock Waves, vol. 17, No. 6, pp. 441-447, 2008.
(Continued)

*Primary Examiner* — Walter D Griffin
*Assistant Examiner* — Cameron Allen
(74) *Attorney, Agent, or Firm* — Rick Klein; Fay Sharpe

(57) ABSTRACT

Acoustophoretic devices and methods for concentrating targeted biological cells in a reduced volume using multi-dimensional acoustic standing waves are disclosed. The methods include flowing a mixture of a host fluid and the biological cells through an acoustophoretic device. The acoustophoretic devices include an inlet, an outlet, and a flow chamber having an ultrasonic transducer-reflector pair. Biological cells, such as T cells, are separated from a host fluid for utilization in allergenic or autologous cell therapies. The disclosed devices and methods are capable of concentrating biological cells to at least 100 times their original cell concentration. The disclosed methods and devices are further capable of decreasing an original feed volume to a final concentrated volume that is less than one percent of the original feed volume.

20 Claims, 24 Drawing Sheets

Related U.S. Application Data application No. 14/026,413, filed on Sep. 13, 2013, now Pat. No. 9,458,450.

(60) Provisional application No. 62/286,986, filed on Jan. 26, 2016.

(51) Int. Cl.
  *C12M 1/00* (2006.01)
  *G10K 15/04* (2006.01)

(58) Field of Classification Search
  CPC ..... B01D 2201/0446; B01D 2201/127; C12M 25/00; C12M 1/12
  See application file for complete search history.

(56) References Cited

U.S. PATENT DOCUMENTS

| | | |
|---|---|---|
| 3,372,370 A | 3/1968 | Cyr |
| 3,555,311 A | 1/1971 | Weber |
| 4,055,491 A | 10/1977 | Porath-Furedi |
| 4,065,875 A | 1/1978 | Srna |
| 4,118,649 A | 10/1978 | Schwartzman et al. |
| 4,158,629 A | 6/1979 | Sawyer |
| 4,165,273 A | 8/1979 | Azarov et al. |
| 4,173,725 A | 11/1979 | Asai et al. |
| 4,204,096 A | 5/1980 | Barcus et al. |
| 4,254,661 A | 3/1981 | Kossoff et al. |
| 4,320,659 A | 3/1982 | Lynnworth et al. |
| 4,344,448 A | 8/1982 | Potts |
| 4,398,325 A | 8/1983 | Piaget et al. |
| 4,552,669 A | 11/1985 | Sekellick |
| 4,666,595 A | 5/1987 | Graham |
| 4,673,512 A | 6/1987 | Schram |
| 4,699,588 A | 10/1987 | Zinn et al. |
| 4,743,361 A | 5/1988 | Schram |
| 4,759,775 A | 7/1988 | Peterson et al. |
| 4,800,316 A | 1/1989 | Wang |
| 4,821,838 A | 4/1989 | Chen |
| 4,836,684 A | 6/1989 | Javorik et al. |
| 4,860,993 A | 8/1989 | Goode |
| 4,878,210 A | 10/1989 | Mitome |
| 4,983,189 A | 1/1991 | Peterson et al. |
| 5,059,811 A | 10/1991 | King et al. |
| 5,062,965 A | 11/1991 | Bernou et al. |
| 5,085,783 A | 2/1992 | Feke et al. |
| 5,164,094 A | 11/1992 | Stuckart |
| 5,225,089 A | 7/1993 | Benes et al. |
| 5,371,729 A | 12/1994 | Manna |
| 5,395,592 A | 3/1995 | Bolleman et al. |
| 5,431,817 A | 7/1995 | Braatz et al. |
| 5,443,985 A | 8/1995 | Lu et al. |
| 5,452,267 A | 9/1995 | Spevak |
| 5,475,486 A | 12/1995 | Paoli |
| 5,484,537 A | 1/1996 | Whitworth |
| 5,527,460 A | 6/1996 | Trampler et al. |
| 5,560,362 A | 10/1996 | Sliwa, Jr. et al. |
| 5,594,165 A | 1/1997 | Madanshetty |
| 5,604,301 A | 2/1997 | Mountford et al. |
| 5,626,767 A | 5/1997 | Trampler et al. |
| 5,688,405 A | 11/1997 | Dickinson et al. |
| 5,711,888 A | 1/1998 | Trampler et al. |
| 5,831,166 A | 11/1998 | Kozuka et al. |
| 5,834,871 A | 11/1998 | Puskas |
| 5,902,489 A | 5/1999 | Yasuda et al. |
| 5,912,182 A | 6/1999 | Coakley et al. |
| 5,947,299 A | 9/1999 | Vazquez et al. |
| 5,951,456 A | 9/1999 | Scott |
| 6,090,295 A | 7/2000 | Raghavarao et al. |
| 6,166,231 A | 12/2000 | Hoeksema |
| 6,205,848 B1 | 3/2001 | Faber et al. |
| 6,216,538 B1 | 4/2001 | Yasuda et al. |
| 6,273,262 B1 | 8/2001 | Yasuda et al. |
| 6,332,541 B1 | 12/2001 | Coakley et al. |
| 6,391,653 B1 | 5/2002 | Letcher et al. |
| 6,475,151 B2 | 11/2002 | Koger et al. |
| 6,482,327 B1 | 11/2002 | Mori et al. |
| 6,487,095 B1 | 11/2002 | Malik et al. |
| 6,592,821 B1 | 7/2003 | Wada et al. |
| 6,641,708 B1 | 11/2003 | Becker et al. |
| 6,649,069 B2 | 11/2003 | DeAngelis |
| 6,699,711 B1 | 3/2004 | Hahn et al. |
| 6,727,451 B1 | 4/2004 | Fuhr et al. |
| 6,763,722 B2 | 7/2004 | Fjield et al. |
| 6,881,314 B1 | 4/2005 | Wang et al. |
| 6,929,750 B2 | 8/2005 | Laurell et al. |
| 6,936,151 B1 | 8/2005 | Lock et al. |
| 7,008,540 B1 | 3/2006 | Weavers et al. |
| 7,010,979 B2 | 3/2006 | Scott |
| 7,061,163 B2 | 6/2006 | Nagahara et al. |
| 7,081,192 B1 | 7/2006 | Wang et al. |
| 7,093,482 B2 | 8/2006 | Berndt |
| 7,108,137 B2 | 9/2006 | Lal et al. |
| 7,150,779 B2 | 12/2006 | Meegan, Jr. |
| 7,186,502 B2 | 3/2007 | Vesey |
| 7,191,787 B1 | 3/2007 | Redeker et al. |
| 7,322,431 B2 | 1/2008 | Ratcliff |
| 7,331,233 B2 | 2/2008 | Scott |
| 7,340,957 B2 | 3/2008 | Kaduchak et al. |
| 7,373,805 B2 | 5/2008 | Hawkes et al. |
| 7,541,166 B2 | 6/2009 | Belgrader et al. |
| 7,601,267 B2 | 10/2009 | Haake et al. |
| 7,673,516 B2 | 3/2010 | Janssen et al. |
| 7,837,040 B2 | 11/2010 | Ward et al. |
| 7,846,382 B2 | 12/2010 | Strand et al. |
| 7,968,049 B2 | 6/2011 | Takahashi et al. |
| 8,075,786 B2 | 12/2011 | Bagajewicz |
| 8,080,202 B2 | 12/2011 | Takahashi et al. |
| 8,134,705 B2 | 3/2012 | Kaduchak et al. |
| 8,256,076 B1 | 9/2012 | Feller |
| 8,266,950 B2 | 9/2012 | Kaduchak et al. |
| 8,273,253 B2 | 9/2012 | Curran |
| 8,273,302 B2 | 9/2012 | Takahashi et al. |
| 8,309,408 B2 | 11/2012 | Ward et al. |
| 8,319,398 B2 | 11/2012 | Vivek et al. |
| 8,334,133 B2 | 12/2012 | Fedorov et al. |
| 8,387,803 B2 | 3/2013 | Thorslund et al. |
| 8,592,204 B2 | 11/2013 | Lipkens et al. |
| 8,679,338 B2 | 3/2014 | Rietman et al. |
| 8,691,145 B2 | 4/2014 | Dionne et al. |
| 8,873,051 B2 | 10/2014 | Kaduchak et al. |
| 8,889,388 B2 | 11/2014 | Wang et al. |
| 9,228,183 B2 * | 1/2016 | Lipkens ............... B01D 21/28 |
| 9,272,234 B2 | 3/2016 | Lipkens et al. |
| 9,357,293 B2 | 5/2016 | Claussen |
| 9,365,815 B2 | 6/2016 | Miyazaki et al. |
| 9,368,110 B1 | 6/2016 | Hershey et al. |
| 9,388,363 B2 | 7/2016 | Goodson et al. |
| 9,391,542 B2 | 7/2016 | Wischnewskiy |
| 9,403,114 B2 | 8/2016 | Kusuura |
| 9,410,256 B2 | 8/2016 | Dionne et al. |
| 9,416,344 B2 | 8/2016 | Lipkens et al. |
| 9,421,553 B2 | 8/2016 | Dionne et al. |
| 9,422,328 B2 | 8/2016 | Kennedy, III et al. |
| 9,457,139 B2 | 10/2016 | Ward et al. |
| 9,457,302 B2 | 10/2016 | Lipkens et al. |
| 9,458,450 B2 | 10/2016 | Lipkens et al. |
| 9,464,303 B2 | 10/2016 | Burke |
| 9,476,855 B2 | 10/2016 | Ward et al. |
| 9,480,375 B2 | 11/2016 | Marshall et al. |
| 9,480,935 B2 | 11/2016 | Mariella, Jr. et al. |
| 9,488,621 B2 | 11/2016 | Kaduchak et al. |
| 9,504,780 B2 | 11/2016 | Spain et al. |
| 9,512,395 B2 | 12/2016 | Lipkens et al. |
| 9,513,205 B2 | 12/2016 | Yu et al. |
| 9,514,924 B2 | 12/2016 | Morris et al. |
| 9,517,474 B2 | 12/2016 | Mao et al. |
| 2002/0038662 A1 | 4/2002 | Schuler et al. |
| 2002/0134734 A1 | 9/2002 | Campbell et al. |
| 2003/0015035 A1 | 1/2003 | Kaduchak et al. |
| 2003/0028108 A1 | 2/2003 | Miller et al. |
| 2003/0195496 A1 | 10/2003 | Maguire |
| 2003/0209500 A1 | 11/2003 | Kock et al. |
| 2003/0230535 A1 | 12/2003 | Affeld et al. |

(56) References Cited

U.S. PATENT DOCUMENTS

| | | |
|---|---|---|
| 2004/0016699 A1 | 1/2004 | Bayevsky |
| 2004/0035208 A1 | 2/2004 | Diaz et al. |
| 2004/0112841 A1 | 6/2004 | Scott |
| 2004/0124155 A1 | 7/2004 | Meegan, Jr. |
| 2004/0149039 A1 | 8/2004 | Cardelius |
| 2005/0031499 A1 | 2/2005 | Meier |
| 2005/0121269 A1 | 6/2005 | Namduri |
| 2005/0145567 A1 | 7/2005 | Quintel et al. |
| 2005/0196725 A1 | 9/2005 | Fu |
| 2006/0037915 A1 | 2/2006 | Strand et al. |
| 2006/0037916 A1 | 2/2006 | Trampler |
| 2006/0050615 A1 | 3/2006 | Swisher |
| 2007/0053795 A1 | 3/2007 | Laugharn, Jr. et al. |
| 2007/0224676 A1 | 9/2007 | Haq |
| 2007/0267351 A1 | 11/2007 | Roach et al. |
| 2007/0272618 A1 | 11/2007 | Gou et al. |
| 2007/0284299 A1 | 12/2007 | Xu et al. |
| 2008/0011693 A1 | 1/2008 | Li et al. |
| 2008/0067128 A1 | 3/2008 | Hoyos et al. |
| 2008/0105625 A1 | 5/2008 | Rosenberg et al. |
| 2008/0181838 A1 | 7/2008 | Kluck |
| 2008/0217259 A1 | 9/2008 | Siversson |
| 2008/0245709 A1 | 10/2008 | Kaduchak et al. |
| 2008/0245745 A1 | 10/2008 | Ward et al. |
| 2008/0264716 A1 | 10/2008 | Kuiper et al. |
| 2008/0272034 A1 | 11/2008 | Ferren et al. |
| 2008/0272065 A1 | 11/2008 | Johnson |
| 2008/0316866 A1 | 12/2008 | Goodemote et al. |
| 2009/0029870 A1 | 1/2009 | Ward et al. |
| 2009/0045107 A1 | 2/2009 | Ward et al. |
| 2009/0053686 A1 | 2/2009 | Ward et al. |
| 2009/0087492 A1 | 4/2009 | Johnson et al. |
| 2009/0098027 A1 | 4/2009 | Tabata et al. |
| 2009/0104594 A1 | 4/2009 | Webb |
| 2009/0126481 A1 | 5/2009 | Burris |
| 2009/0178716 A1 | 7/2009 | Kaduchak et al. |
| 2009/0194420 A1 | 8/2009 | Mariella, Jr. et al. |
| 2009/0227042 A1 | 9/2009 | Gauer et al. |
| 2009/0295505 A1 | 12/2009 | Mohammadi et al. |
| 2010/0000945 A1 | 1/2010 | Gavalas |
| 2010/0078323 A1 | 4/2010 | Takahashi et al. |
| 2010/0078384 A1 | 4/2010 | Yang |
| 2010/0124142 A1 | 5/2010 | Laugharn et al. |
| 2010/0139377 A1 | 6/2010 | Huang et al. |
| 2010/0192693 A1 | 8/2010 | Mudge et al. |
| 2010/0193407 A1 | 8/2010 | Steinberg et al. |
| 2010/0206818 A1 | 8/2010 | Leong et al. |
| 2010/0255573 A1 | 10/2010 | Bond et al. |
| 2010/0261918 A1 | 10/2010 | Chianelli et al. |
| 2010/0317088 A1 | 12/2010 | Radaelli et al. |
| 2010/0323342 A1 | 12/2010 | Gonzalez Gomez et al. |
| 2010/0330633 A1 | 12/2010 | Walther et al. |
| 2011/0003350 A1 | 1/2011 | Schafran et al. |
| 2011/0024335 A1 | 2/2011 | Ward et al. |
| 2011/0092726 A1 | 4/2011 | Clarke |
| 2011/0095225 A1 | 4/2011 | Eckelberry et al. |
| 2011/0123392 A1 | 5/2011 | Dionne et al. |
| 2011/0125024 A1 | 5/2011 | Mueller |
| 2011/0146678 A1 | 6/2011 | Ruecroft et al. |
| 2011/0154890 A1 | 6/2011 | Holm et al. |
| 2011/0166551 A1 | 7/2011 | Schafer |
| 2011/0189732 A1 | 8/2011 | Weinand et al. |
| 2011/0245750 A1 | 10/2011 | Lynch et al. |
| 2011/0262990 A1 | 10/2011 | Wang et al. |
| 2011/0278218 A1 | 11/2011 | Dionne et al. |
| 2011/0281319 A1 | 11/2011 | Swayze et al. |
| 2011/0309020 A1 | 12/2011 | Rietman et al. |
| 2012/0088295 A1 | 4/2012 | Yasuda et al. |
| 2012/0145633 A1 | 6/2012 | Polizzotti et al. |
| 2012/0163126 A1 | 6/2012 | Campbell et al. |
| 2012/0175012 A1 | 7/2012 | Goodwin et al. |
| 2012/0231504 A1 | 9/2012 | Niazi |
| 2012/0267288 A1 | 10/2012 | Chen et al. |
| 2012/0325727 A1 | 12/2012 | Dionne et al. |
| 2012/0325747 A1 | 12/2012 | Reitman et al. |
| 2012/0328477 A1 | 12/2012 | Dionne et al. |
| 2012/0329122 A1 | 12/2012 | Lipkens et al. |
| 2013/0017577 A1 | 1/2013 | Arunakumari et al. |
| 2013/0115664 A1 | 5/2013 | Khanna et al. |
| 2013/0175226 A1 | 7/2013 | Coussios et al. |
| 2013/0217113 A1 | 8/2013 | Srinivasan et al. |
| 2013/0277316 A1 | 10/2013 | Dutra et al. |
| 2013/0277317 A1 | 10/2013 | LoRicco et al. |
| 2013/0284271 A1 | 10/2013 | Lipkens et al. |
| 2014/0011240 A1* | 1/2014 | Lipkens ............... B01D 21/28 435/71.1 |
| 2014/0017758 A1 | 1/2014 | Kniep et al. |
| 2014/0102947 A1 | 4/2014 | Baym et al. |
| 2014/0141413 A1 | 5/2014 | Laugham, Jr. et al. |
| 2014/0319077 A1 | 10/2014 | Lipkens et al. |
| 2014/0377834 A1 | 12/2014 | Presz, Jr. et al. |
| 2015/0053561 A1 | 2/2015 | Ward et al. |
| 2015/0060581 A1 | 3/2015 | Santos et al. |
| 2015/0209695 A1* | 7/2015 | McCarthy ............ B01D 21/28 210/748.05 |
| 2015/0321129 A1 | 11/2015 | Lipkens et al. |
| 2016/0121331 A1 | 5/2016 | Kapur et al. |
| 2016/0123858 A1 | 5/2016 | Kapur et al. |
| 2016/0145563 A1 | 5/2016 | Berteau et al. |
| 2016/0153249 A1 | 6/2016 | Mitri |
| 2016/0175198 A1 | 6/2016 | Warner et al. |
| 2016/0184790 A1 | 6/2016 | Sinha et al. |
| 2016/0202237 A1 | 7/2016 | Zeng et al. |
| 2016/0208213 A1 | 7/2016 | Doyle et al. |
| 2016/0230168 A1 | 8/2016 | Kaduchak et al. |
| 2016/0237110 A1 | 8/2016 | Gilmanshin et al. |
| 2016/0237394 A1 | 8/2016 | Lipkens et al. |
| 2016/0237395 A1 | 8/2016 | Lipkens et al. |
| 2016/0252445 A1 | 9/2016 | Yu et al. |
| 2016/0279540 A1 | 9/2016 | Presz, Jr. et al. |
| 2016/0279551 A1 | 9/2016 | Foucault |
| 2016/0312168 A1 | 10/2016 | Pizzi |
| 2016/0314868 A1 | 10/2016 | El-Zahab et al. |
| 2016/0319270 A1 | 11/2016 | Lipkens et al. |
| 2016/0325206 A1 | 11/2016 | Presz, Jr. et al. |
| 2016/0332159 A1 | 11/2016 | Dual et al. |
| 2016/0339360 A1 | 11/2016 | Lipkens et al. |
| 2016/0347628 A1 | 12/2016 | Dionne et al. |
| 2016/0355776 A1 | 12/2016 | Lipkens et al. |
| 2016/0361670 A1 | 12/2016 | Lipkens et al. |
| 2016/0363579 A1 | 12/2016 | Lipkens et al. |
| 2017/0044517 A1* | 2/2017 | Lipkens ............... C12N 13/00 |

FOREIGN PATENT DOCUMENTS

| | | |
|---|---|---|
| DE | 196 48 519 A1 | 6/1998 |
| DE | 103 19 467 B3 | 7/2004 |
| DE | 10 2008 006 501 A1 | 9/2008 |
| EP | 0 292 470 B1 | 11/1988 |
| EP | 0 641 606 | 3/1995 |
| EP | 1 175 931 A1 | 1/2002 |
| EP | 1 254 669 B1 | 11/2002 |
| GB | 2 420 510 A | 5/2006 |
| JP | 9-136090 | 5/1997 |
| RU | 2085933 | 7/1997 |
| SU | 629496 | 10/1978 |
| WO | WO 87/07178 A1 | 12/1987 |
| WO | WO 89/11899 A1 | 12/1989 |
| WO | WO 90/05008 | 3/1990 |
| WO | WO 97/34643 | 9/1997 |
| WO | WO 98/17373 | 4/1998 |
| WO | WO 98/50133 A1 | 11/1998 |
| WO | WO 02/072234 A1 | 9/2002 |
| WO | WO 03/089567 | 10/2003 |
| WO | WO 2004/079716 A1 | 9/2004 |
| WO | WO 2009/063198 | 5/2009 |
| WO | WO 2009/111276 A1 | 9/2009 |
| WO | WO 2009/144709 A1 | 12/2009 |
| WO | WO 2010/024753 A1 | 4/2010 |
| WO | WO 2010/040394 A1 | 4/2010 |
| WO | WO 2011/023949 A2 | 3/2011 |
| WO | WO 2011/025890 A1 | 3/2011 |
| WO | WO 2011/027146 A2 | 3/2011 |
| WO | WO 2011/131947 A2 | 10/2011 |

(56) References Cited

FOREIGN PATENT DOCUMENTS

| WO | WO 2011/161463 A2 | 12/2011 |
|---|---|---|
| WO | WO 2013/043297 A1 | 3/2013 |
| WO | WO 2013/055517 A1 | 4/2013 |
| WO | WO 2013/138797 A1 | 9/2013 |
| WO | WO 2013/148376 | 10/2013 |
| WO | WO 2013/159014 A1 | 10/2013 |
| WO | WO 2014/014941 A1 | 1/2014 |
| WO | WO 2014/029505 | 2/2014 |
| WO | WO 2014/055219 A2 | 4/2014 |
| WO | WO 2014/124306 A1 | 8/2014 |
| WO | WO 2014/153651 | 10/2014 |
| WO | WO 2015/006730 | 1/2015 |

OTHER PUBLICATIONS

Benes et al.; Ultrasonic Separation of Suspended Particles, 2001 IEEE Ultrasonics Symposium; Oct. 7-10, 2001; pp. 649-659; Atlanta, Georgia.
Castilho et al.; Animal Cell Technology: From Biopharmaceuticals to Gene Therapy; 11—Animal Cell Separation; 2008.
Castro; Tunable gap and quantum quench dynamics in bilayer graphene; Jul. 13, 2010; Mathematica Summer School.
Cravotto et al.; Ultrasonics Sonochemistry, vol. 15, No. 5, pp. 898-902, 2008.
Garcia-Lopez, et al; Enhanced Acoustic Separation of Oil-Water Emulsion in Resonant Cavities. The Open Acoustics Journal. 2008, vol. 1, pp. 66-71.
Hill et al.; Ultrasonic Particle Manipulation; Microfluidic Technologies for Miniaturized Analysis Systems, Jan. 2007, pp. 359-378.
Ilinskii et al.; Acoustic Radiation Force on a Sphere in Tissue; AIP Conference Proceedings; 2012.
Kuznetsova et al.; Microparticle concentration in short path length ultrasonic resonators: Roles of radiation pressure and acoustic streaming; Journal of the Acoustical Society of America, American Institute of Physics for the Acoustical Society of America, vol. 116, No. 4, Oct. 1, 2004, pp. 1956-1966, DOI: 1.1121/1.1785831.
Latt et al.; Ultrasound-membrane hybrid processes for enhancement of filtration properties; Ultrasonics sonochemistry 13.4 (2006): 321-328.
Li et al.; Electromechanical behavior of PZT-brass unimorphs; J. Am. Ceram. Soc. vol. 82; No. 7; pp. 1733-1740, 1999.
Lipkens et al.; Frequency sweeping and fluid flow effects on particle trajectories in ultrasonic standing waves; Acoustics 08, Paris, Jun. 29-Jul. 4, 2008.
Lipkens et al.; Prediction and measurement of particle velocities in ultrasonic standing waves; J. Acoust. Soc. Am., 124 No. 4, pp. 2492 (A) 2008.
Lipkens et al.; Separation of micron-sized particles in macro-scale cavities by ultrasonic standing waves; Presented at the International Congress on Ultrasonics, Santiago; Jan. 11-17, 2009.
Lipkens et al.; The effect of frequency sweeping and fluid flow on particle trajectories in ultrasonic standing waves; IEEE Sensors Journal, vol. 8, No. 6, pp. 667-677, 2008.
Lipkens et al.; Separation of bacterial spores from flowering water in macro-scale cavities by ultrasonic standing waves; submitted/uploaded to http://arxiv.org/abs/1006.5467 on Jun. 28, 2010.
Lipkens et al., Macro-scale acoustophoretic separation of lipid particles from red blood cells, The Journal of the Acoustical Society of America, vol. 133, Jun. 2, 2013, p. 045017, XP055162509, New York, NY.
Meribout et al.; An Industrial-Prototype Acoustic Array for Real-Time Emulsion Layer Detection in Oil Storage Tanks; IEEE Sensors Journal, vol. 9, No. 12, Dec. 2009.
Nilsson et al.; Review of cell and particle trapping in microfluidic systems; Department of Measurement Technology and Industrial Electrical Engineering, Div. of Nanobiotechnology, Lund University, P.O. Box 118. Lund, Sweden, Analytica Chimica Acta 649, Jul. 14, 2009, pp. 141-157.

Pangu et al.; Droplet transport and coalescence kinetics in emulsions subjected to acoustic fields; Ultrasonics 46, pp. 289-302 (2007).
Ponomarenko et al.; Density of states and zero Landau level probed through capacitance of graphene; Nature Nanotechnology Letters, Jul. 5, 2009; DOI: 10.1038/NNANO.2009.177.
Ryll et al.; Performance of Small-Scale CHO Perfusion Cultures Using an Acoustic Cell Filtration Device for Cell Retention: Characterization of Separation Efficiency and Impact of Perfusion on Product Quality; Biotechnology and Bioengineering; vol. 69; Iss. 4; pp. 440-449; Aug. 2000.
Seymour et al, J. Chem. Edu., 1990, 67(9), p. 763, published Sep. 1990.
Volpin et al.; Mesh simplification with smooth surface reconstruction; Computer-Aided Design; vol. 30; No. 11; 1998.
Wang et al.; Retention and Viability Characteristics of Mammalian Cells in an Acoustically Driven Polymer Mesh; Biotechnol. Prog. 2004, pp. 384-387 (2004).
Wicklund et al.; Ultrasonic Manipulation of Single Cells; Methods in Molecular Biology; vol. 853; pp. 1777-196; 2012.
Annex to Form PCT/ISA/206—Communication Relating to the Results of the Partial International Search Report, dated Jul. 18, 2013.
European Search Report of European Application No. 11769474.5, dated Sep. 5, 2013.
European Search Report of European Application No. 13760840.2, dated Feb. 4, 2016.
European Search Report of European Application No. 13721179.3 dated Feb. 23, 2016.
International Search Report and Written Opinion dated Dec. 20, 2011, for corresponding PCT application No. PCT/US2011/032181.
International Search Report and Written Opinion dated Feb. 27, 2012, for PCT application No. PCT/US2011/040787.
International Search Report and Written Opinion of International Application No. PCT/US2012/051804 dated Nov. 16, 2012.
International Search Report and Written Opinion of International Application No. PCT/US2013/037404 Dated Jun. 21, 2013.
International Search Report and Written Opinion of International Application No. PCT/US2013/032705 dated Jul. 26, 2013.
International Search Report and Written Opinion of International Application No. PCT/US2013/050729 Dated Sep. 25, 2013.
International Search Report dated Feb. 18, 2014 in corresponding PCT Application No. PCT/US2013/059640.
International Search Report for corresponding PCT Application Serial No. PCT/US2014/015382 dated May 6, 2014.
International Search Report for PCT/US2014/035557 dated Aug. 27, 2014.
International Search Report for PCT/US2014/043930 dated Oct. 22, 2014.
International Search Report for PCT/US2014/046412 dated Oct. 27, 2014.
International Search Report for PCT/US2014/064088 dated Jan. 30, 2015.
Extended European Search Report for Application No. EP 12833859.7 dated Mar. 20, 2015.
International Search Report and Written Opinion for International Application No. PCT/US2015/010595 dated Apr. 15, 2015.
International Search Report for PCT/US2015/019755 dated May 4, 2015.
International Search Report mailed Jul. 30, 2015 for International Application No. PCT/US2015/030009.
International Search Report for PCT/US2015/039125 dated Sep. 30, 2015.
International Search Report and Written Opinion for PCT Application Serial No. PCT/US2015/053200 dated Dec. 28, 2015.
European Search Report of European Application No. 11796470.0 dated Jan. 5, 2016.
International Search Report and Written Opinion for International Application No. PCT/US2015/066884, dated Mar. 22, 2016.
International Search Report and Written Opinion for International Application No. PCT/US2016/024082 dated Jun. 27, 2016.
International Search Report and Written Opinion for International Application No. PCT/US2016/044586 dated Oct. 21, 2016.

(56) References Cited

OTHER PUBLICATIONS

International Search Report and Written Opinion for International Application No. PCT/US2016/031357 dated Jul. 26, 2016.
International Search Report and Written Opinion for International Application No. PCT/US2015/024365 dated Oct. 13, 2016.
International Search Report and Written Opinion for International Application No. PCT/US2016/041664 dated Oct. 18, 2016.
International Search Report and Written Opinion for International Application No. PCT/US2016/049088 dated Nov. 28, 2016.
International Search Report and Written Opinion for International Application No. PCT/US2016/050415 dated Nov. 28, 2016.
International Search Report and Written Opinion for International Application No. PCT/US2016/037104 dated Dec. 16, 2016.
Phys. Org. "Engineers develop revolutionary nanotech water desalination membrane." Nov. 6, 2006. http://phys.org/news82047372.html.
"Proceedings of the Acoustics 2012 Nantes Conference," Apr. 23-27, 2012, Nantes, France, pp. 278-282.
Sony New Release: <http://www.sony.net/SonyInfo/News/Press/201010/10-137E/index.html>.

\* cited by examiner

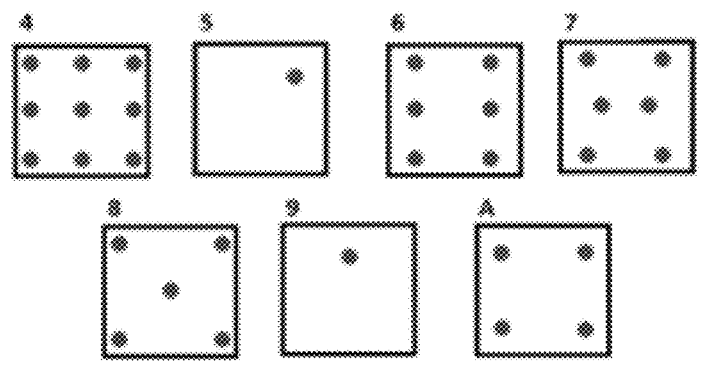
FIG. 25A
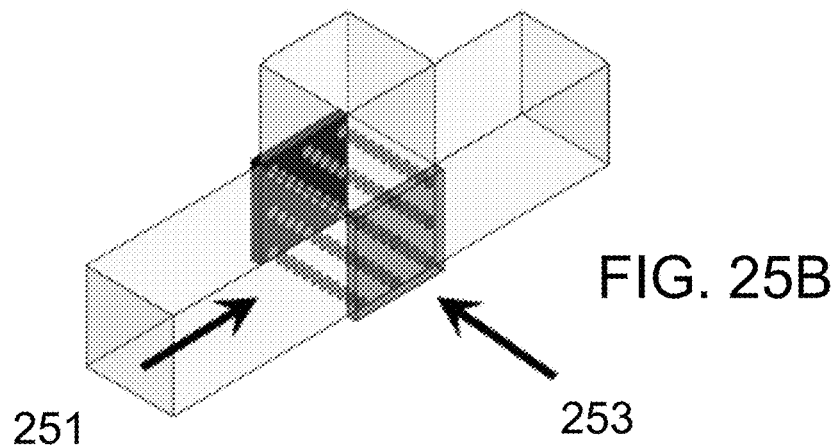
FIG. 25B
251          253
FIG. 25C              FIG. 25D
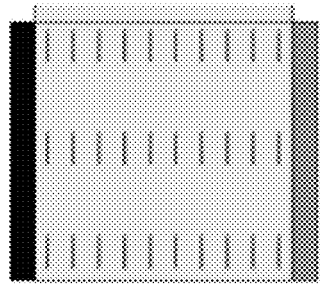 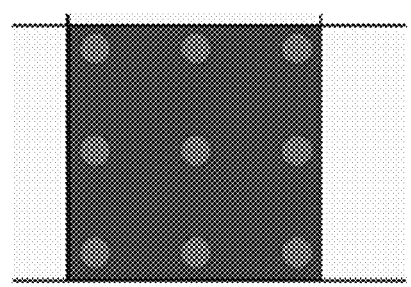

SYSTEM FOR GENERATING HIGH CONCENTRATION FACTORS FOR LOW CELL DENSITY SUSPENSIONS

CROSS-REFERENCE TO RELATED APPLICATIONS

This application claims priority to U.S. Provisional Patent Application Ser. No. 62/286,986, filed on Jan. 26, 2016. This application is also a continuation-in-part of U.S. patent application Ser. No. 15/285,434, filed Oct. 4, 2016, which is a continuation of U.S. Ser. No. 14/026,413, filed Sep. 13, 2013, now U.S. Pat. No. 9,458,450. These applications are incorporated herein by reference in their entireties.

BACKGROUND

Many therapeutic biological cells are present in very low concentrations in human body fluids. This low concentration is true for both autologous and allergenic cell collection. Such cells, even when produced via industrial biotechnological processes, are still present in very low concentrations.

T cells, named as such because they mature in the thymus, have been found to play an intricate role in the immune system and disease prevention. For instance, one special type of T cell is known as a Jurkat T cell. This cell line is an immortalized line of cells that are used to study T cell leukemia, T cell signaling, and other types of diseases, particularly HIV. Recently, T cells for various therapies have been collected and concentrated. One of the targeted therapies is the use of transfected T cells for cancer treatments. These types of cells have become an area of great interest for disease prevention, including cancer, in recent scientific investigations.

Conventional means for separating desirable cells from other materials include centrifugation and physical filter (size exclusion) processes. During these physical separation processes, many of the desirable cells are damaged or destroyed. Additionally, the low concentration of such cells reduces the efficiency of industrial processes. Low T cell concentration makes efficacy of therapeutic treatments difficult.

BRIEF DESCRIPTION

The present disclosure relates, in various embodiments, to acoustophoretic systems, devices, and methods using multi-dimensional acoustic standing waves to concentrate particles in a host fluid, namely target cells such as biological cells (e.g., Chinese hamster ovary (CHO) cells, NSO hybridoma cells, baby hamster kidney (BHK) cells, or human cells, T cells, B cells, NK cells, algae, bacteria, viruses, or microcarriers). More particularly, the devices include a flow chamber implemented with an ultrasonic transducer and reflector that set up a multi-dimensional acoustic standing wave.

Disclosed herein are methods for concentrating target cells having an original cell concentration in a host fluid. The methods comprise flowing a mixture of the host fluid and the target cells through an acoustophoretic device, which can be constructed as described herein, and driving the at least one ultrasonic transducer, such as with a voltage signal, to create the multi-dimensional standing wave, such that the target cells are concentrated in the multi-dimensional acoustic standing wave to a final concentration of at least 100 times their original cell concentration. The acoustophoretic device includes a flow chamber having an inlet and an outlet; at least one ultrasonic transducer coupled to the flow chamber to permit a multi-dimensional acoustic standing wave to be generated in the flow chamber by the at least one ultrasonic transducer. The at least one transducer includes a piezoelectric material configured to be driven to create a multi-dimensional acoustic standing wave in the flow chamber. The piezoelectric material may be driven or excited by an electrical signal. The electrical signal may be controlled based on voltage, current, frequency, phase or any other suitable characteristics for driving the transducer. A reflector across the flow chamber from the at least one ultrasonic transducer may be provided to reflect an ultrasonic signal to contribute to generating the multi-dimensional acoustic standing wave in the flow chamber. Two opposing ultrasonic transducers may be used to generate the multi-dimensional acoustic standing wave. An ultrasonic transducer may be used to generate an acoustic wave, as well as to reflect an acoustic wave, which can contribute to generating the multi-dimensional acoustic standing wave.

In particular embodiments, the target cells are concentrated to a final concentration of about 150 times to about 300 times their original cell concentration. In other embodiments, the target cells are concentrated to a final concentration of about 300 times to about 600 times their original cell concentration. The target cells can have an original cell concentration of about 1 million cells per mL.

The mixture of the host fluid and the target cells can have an original feed volume of from about 450 mL to about 1800 mL. The original feed volume can be decreased to a final concentrated volume of less than about 10 mL, including between about 3 mL and about 5 mL.

The original feed volume can be reduced by a volume concentration factor of from about 150 to about 600, where the volume concentration factor is defined as the original feed volume divided by the final concentrated volume.

A final concentrated volume can be recovered from the flow chamber after operation of the multi-dimensional acoustic standing wave, containing the concentrated cells. The total cell retention in the final concentrated volume can be at least 40%, where the total cell retention is defined by the amount of cells retained within the final concentration volume divided by the total number of cells introduced into the flow chamber. The total cell retention can also be at least 80%, or at least 90%.

In certain embodiments, the acoustophoretic device is vertically oriented, such that the mixture flows vertically upwards from the at least one inlet toward the at least one outlet.

The at least one inlet can be located at a first end of the device along a first side thereof, and the at least one outlet can be located at a second end of the device opposite the first end thereof.

The acoustophoretic device can further comprise a collector located between the at least one inlet and the at least one ultrasonic transducer. The collector can include at least one angled wall. The at least one outlet of the acoustophoretic device can include a permeate outlet located at the top end of the device and a concentrate outlet located between the at least one inlet and the collector, wherein the at least one angled wall of the collector leads to the concentrate outlet.

The inlets may be located on a side of the device. This location causes the mixture entering the device through the at least one inlet to flow through an annular plenum around the collector. This configuration may cause the mixture to make a sharp turn. In particular embodiments, the concentrate outlet is located on a first side of the device.

The multi-dimensional acoustic standing wave can continuously trap the biological cells therein, such that the target cells agglomerate, aggregate, clump, or coalesces together, and subsequently settle out of the host fluid and into the collector due to enhanced gravitational forces. As the target cells settle out of the host fluid, they fall downwards onto the at least one angled wall of the collector.

The at least one ultrasonic transducer of the acoustophoretic device can include a plurality of ultrasonic transducers arranged serially between the at least one inlet and the at least one outlet of the acoustophoretic device.

Also disclosed are methods for obtaining concentrated target cells, comprising flowing an original feed volume of a mixture of a host fluid and the target cells through an acoustophoretic device, which results in concentration of the target cells. Desirably, at least 40% the concentrated target cells in the original feed volume are recovered in a final concentrated volume, wherein the final concentrated volume is at least 100 times smaller than the original feed volume.

Acoustophoresis devices are also disclosed. The devices comprise: at least one inlet at a first end of the device; a concentrate outlet on a first side of the device; a flow chamber fluidly connected to the at least one inlet and the concentrate inlet; at least one ultrasonic transducer coupled to a side of the flow chamber, the at least one ultrasonic transducer including a piezoelectric material that can be driven to create a multi-dimensional acoustic standing wave in the flow chamber; a reflector coupled to an opposite side of the flow chamber from the at least one ultrasonic transducer; and a collector located between the at least one inlet and the at least one ultrasonic transducer, the collector including at least one angled wall that tapers downwards in cross-sectional area, the collector being fluidly connected to the concentrate outlet.

In particular embodiments, the at least one inlet of the acoustophoretic device is located at a first end of the acoustophoretic device; and the device further comprises a permeate outlet located at a second end of the device opposite the first end.

The device may also include an annular plenum around the collector fluidly connecting the at least one inlet to the flow chamber.

In particular embodiments, the multi-dimensional standing wave results in an acoustic radiation force having an axial force component and a lateral force component that are the same order of magnitude.

These and other non-limiting characteristics are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

FIG. 25A illustrates the trapping line configurations for seven peak amplitudes of an ultrasonic transducer of the present disclosure. FIG. 25B is a perspective view generally illustrating a device of the present disclosure. The fluid flow direction and the trapping lines are shown. FIG. 25C is a view from the fluid inlet along the fluid flow direction (arrow 251) of FIG. 25B, showing the trapping nodes of the standing wave where particles would be captured. FIG. 25D is a view taken through the transducers face at the trapping line configurations, along arrow 253 as shown in FIG. 25B.

DETAILED DESCRIPTION

Figure 1:
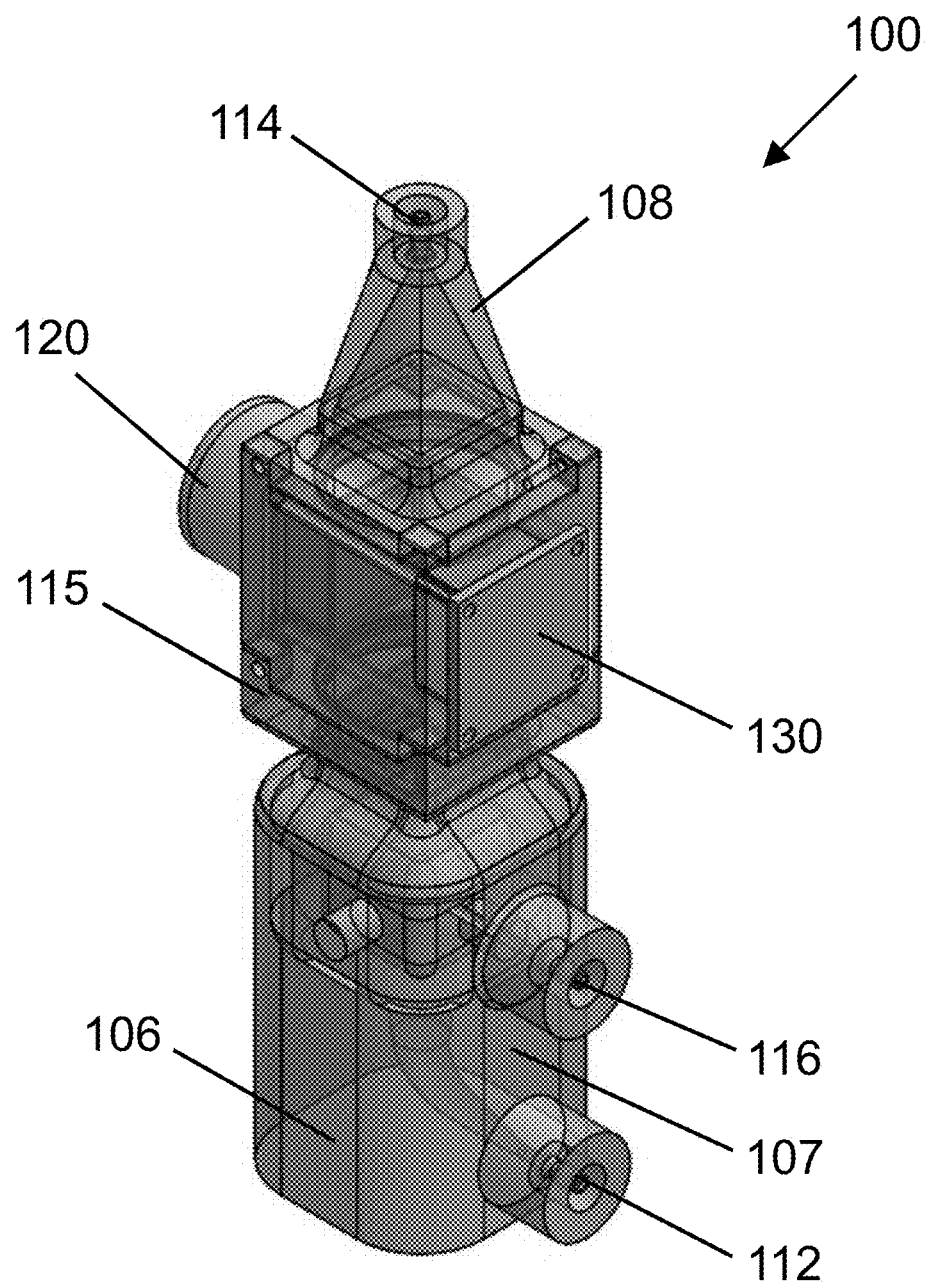
FIG. 1 is a perspective view of an exemplary acoustophoretic device according to the present disclosure.

The present disclosure may be understood more readily by reference to the following detailed description of desired embodiments and the examples included therein. In the following specification and the claims which follow, reference will be made to a number of terms which shall be defined to have the following meanings.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

The term "comprising" is used herein as requiring the presence of the named component and allowing the presence of other components. The term "comprising" should be construed to include the term "consisting of", which allows the presence of only the named component, along with any impurities that might result from the manufacture of the named component.

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values). The endpoints of the ranges and any values disclosed herein are not limited to the precise range or value; they are sufficiently imprecise to include values approximating these ranges and/or values.

The modifier "about" used in connection with a quantity is inclusive of the stated value and has the meaning dictated by the context. When used in the context of a range, the modifier "about" should also be considered as disclosing the range defined by the absolute values of the two endpoints. For example, the range of "from about 2 to about 10" also discloses the range "from 2 to 10." The term "about" may refer to plus or minus 10% of the indicated number. For example, "about 10%" may indicate a range of 9% to 11%, and "about 1" may mean from 0.9-1.1.

It should be noted that many of the terms used herein are relative terms. For example, the terms "upper" and "lower" are relative to each other in location, i.e. an upper component is located at a higher elevation than a lower component in a given orientation, but these terms can change if the device is flipped. The terms "inlet" and "outlet" are relative to a fluid flowing through them with respect to a given structure, e.g. a fluid flows through the inlet into the structure and flows through the outlet out of the structure. The terms "upstream" and "downstream" are relative to the direction in which a fluid flows through various components, i.e. the flow fluids through an upstream component prior to flowing through the downstream component. It should be noted that in a loop, a first component can be described as being both upstream of and downstream of a second component.

The terms "horizontal" and "vertical" are used to indicate direction relative to an absolute reference, i.e. ground level. However, these terms should not be construed to require structures to be absolutely parallel or absolutely perpendicular to each other. For example, a first vertical structure and a second vertical structure are not necessarily parallel to each other. The terms "top" and "bottom" or "base" are used to refer to surfaces where the top is always higher than the bottom/base relative to an absolute reference, i.e. the surface of the earth. The terms "upwards" and "downwards" are also relative to an absolute reference; upwards is always against the gravity of the earth.

The term "parallel" should be construed in its lay sense of two surfaces that maintain a generally constant distance between them, and not in the strict mathematical sense that such surfaces will never intersect when extended to infinity.

The present application may refer to "the same order of magnitude." Two numbers are of the same order of magnitude if the quotient of the larger number divided by the smaller number is a value of at least 1 and less than 10.

Acoustophoresis is a low-power, no-pressure-drop, no-clog, solid-state approach to particle removal from fluid dispersions: i.e., it is used to achieve separations that are more typically performed with porous filters, but it has none of the disadvantages of filters. In particular, the acoustophoretic devices of the present disclosure are suitable for use with bioreactors and operate at the macro-scale for separations in flowing systems with high flow rates. The acoustophoretic devices are designed to create a high intensity multi-dimensional ultrasonic standing wave that results in an acoustic radiation force that is larger than the combined effects of fluid drag and buoyancy or gravity, and is therefore able to trap (i.e., hold stationary) the suspended phase (i.e. cells) to allow more time for the acoustic wave to increase particle concentration, agglomeration and/or coalescence. This feature is an important distinction from previous approaches where particle trajectories were merely altered by the effect of the acoustic radiation force. As a result, in the present devices, the radiation force acts as a filter that prevents targeted particles (e.g., biological cells) from crossing the plane of the standing wave. The trapping capability of a standing wave may be varied as desired, for example by varying the flow rate of the fluid, the acoustic radiation force, and the shape of the acoustophoretic device to maximize cell retention through trapping and settling. This technology offers a green and sustainable alternative for separation of secondary phases with a significant reduction in cost of energy. Excellent particle separation efficiencies have been demonstrated for particle sizes as small as one micron. The acoustophoretic devices of the present disclosure have the ability to create ultrasonic standing wave fields that can trap particles in flow fields with a linear velocity ranging from 0.1 mm/sec to velocities exceeding 1 cm/s.

Generally, an acoustic standing wave generates pressure minima at locations on the standing wave where the amplitude is minimum and maximum. These are called, respectively, nodes and anti-nodes. These pressure minima nodes and anti-nodes may be utilized to capture materials that are differentiated from the surrounding environment by size, density and compressibility (i.e., the speed of sound through the material). Those materials that collect at the pressure minima nodes are known as having a positive contrast factor. Those materials that collect at the pressure minima anti-nodes are known as having a negative contrast factor.

In a typical experiment, the system is operated at a voltage such that the particles are trapped in the ultrasonic standing wave, i.e., remain in a stationary position. The axial component of the acoustic radiation force drives the particles, with a positive contrast factor, to the pressure nodal planes, whereas particles with a negative contrast factor are driven to the pressure anti-nodal planes. The radial or lateral component of the acoustic radiation force contributes to trapping the particle. The forces acting on the particle may be greater than the combined effect of fluid drag force and gravitational force. For small particles or emulsions, the drag force $F_D$ can be expressed as:

$$\vec{F}_D = 4\pi\mu_f R_P(\overline{U}_f - \overline{U}_p)\left[\frac{1 + \frac{3}{2}\hat{\mu}}{1 + \hat{\mu}}\right] \quad (1)$$

where $U_f$ and $U_p$ are the fluid and particle velocity, $R_p$ is the particle radius, $\mu_f$ and $\mu_p$ are the dynamic viscosity of the fluid and particle, and $\hat{\mu}=\mu_p/\mu_f$ is the ratio of dynamic viscosities. The buoyancy force $F_B$ is expressed as:

$$F_B = 4/3\pi R_p^3(\rho_f - \rho_p)g \quad (2)$$

where $R_p$ is the particle radius, $\rho_f$ is the fluid density, $\rho_p$ is the particle density, and g is the universal gravitational constant.

For a particle to be trapped in the ultrasonic standing wave, the force balance on the particle can be assumed to be zero, and therefore an expression for lateral acoustic radiation force $F_{LRF}$ can be found, which is given by:

$$F_{LRF} = F_D + F_B \quad (3)$$

For a particle of known size and material property, and for a given flow rate, this equation can be used to estimate the magnitude of the lateral acoustic radiation force.

The theoretical model that is used to calculate the acoustic radiation force is the formulation developed by Gor'kov, where the primary acoustic radiation force $F_R$ is defined as a function of a field potential U, $F_R = -\nabla(U)$, where the field potential U is defined as $$U = V_o\left[\frac{\langle p^2(x, y, z)\rangle}{2\rho_f c_f^2}f_1 - \frac{3\rho_f\langle v^2(x, y, z)\rangle}{4}f_2\right] \quad (4)$$

and $f_1$ and $f_2$ are the monopole and dipole contributions defined by $$f_1 = 1 - \frac{1}{\Lambda\sigma^2} \quad f_2 = \frac{2(\Lambda - 1)}{2\Lambda + 1} \quad (5)$$

where $$\sigma = \frac{c_p}{c_f} \quad \Lambda = \frac{\rho_p}{\rho_f} \quad \beta_f = \frac{1}{\rho_f c_f^2} \quad (6)$$

where p is the acoustic pressure, u is the fluid particle velocity, $\Lambda$ is the ratio of cell density $\rho_p$ to fluid density $\rho_f$, $\sigma$ is the ratio of cell sound speed $c_p$ to fluid sound speed $c_f$, $V_o=\pi R_p^3$ is the volume of the cell, and < > indicates time averaging over the period of the wave.

For a one dimensional standing wave, where the acoustic pressure is expressed as $$p = A\cos(kx)\cos(\omega t) \quad (7)$$

where A is the acoustic pressure amplitude, k is the wavenumber, and w is the angular frequency. In this case, there is only the axial component of the acoustic radiation force $F_{ARF}$, which is found to be $$F_{ARF} = V_o kX\frac{A^2}{4\rho_f c_f^2}\sin(2kx) \quad (8)$$

where X is the contrast factor given by $$X = \left(\frac{5\Lambda - 2}{1 + 2\Lambda} - \frac{1}{\sigma^2\Lambda}\right) \quad (9)$$

Particles with a positive contrast factor will be driven to the pressure nodal planes, and particles with a negative contrast factor will be driven to the pressure anti-nodal planes. In this way, the generation of a multi-dimensional acoustic standing wave in a flow chamber results in the creation of tightly packed clusters of particles in the flow chamber, typically corresponding to the location of the pressure nodes or anti-nodes in the standing wave depending on acoustic contrast factor.

Gork'ov's model is for a single particle in a standing wave and is limited to particle sizes that are small with respect to the wavelength of the sound fields in the fluid and the particle. It also does not take into account the effect of viscosity of the fluid and the particle on the radiation force. As a result, this model cannot be used for the macro-scale ultrasonic separators discussed herein since particle clusters can grow quite large. A more complex and complete model for acoustic radiation forces without any restriction as to particle size relative to wavelength was therefore used. The models that were implemented are based on the theoretical work of Yurii Ilinskii and Evgenia Zabolotskaya as described in AIP Conference Proceedings, Vol. 1474-1, pp. 255-258 (2012) and "Acoustic radiation force of a sphere without restriction to axisymmetric fields," Proceedings of Meetings on Acoustics, Vol. 19, 045004 (2013). These models also include the effect of fluid and particle viscosity, and therefore are a more accurate calculation of the acoustic radiation force.

The density of a cell type is typically dependent upon the organelles that are enclosed within the cell wall. One type of organelle, the ribosome, is particularly dense. High concentration of ribosomes in cells can thus allow for a high contrast factor between the cell and its fluid medium, and thus allow for excellent differentiation and separation by an acoustic standing wave. However, cells with low ribosomal content, such as Jurkat T cells, present a lower contrast factor and thus can be harder to distinguish, acoustically, from the fluid medium in which they are carried.

Cells that have a low contrast factor compared to the fluid in which they are transported are more difficult to separate using an acoustic standing wave. Through specialized perturbations of a piezoelectric material, higher order modes of vibration in the piezoelectric material may be generated. When this piezoelectric material that is perturbed in a multimode fashion is coupled with a reflector, a specialized type of acoustic standing wave, known as a multi-dimensional acoustic standing wave, is generated. In this way, target biological cells having low cell concentrations (e.g., T cells) may be separated from a fluid medium utilizing a multi-dimensional acoustic standing wave. The target biological cells are generally at lower concentrations than, for example, a CHO cell population with 30 million cells per mL versus a concentration of 1 million cells per mL for Jurkat T cells. Thus, the low contrast cells, such as Jurkat T cells, in a low population concentration are separated continuously from the fluid media within which they are entrained by utilizing a multi-dimensional acoustic standing wave.

The lateral force of the total acoustic radiation force (ARF) generated by the ultrasonic transducers of the present disclosure is significant and is sufficient to overcome the fluid drag force at linear velocities of up to 1 cm/s and beyond. This lateral ARF can thus be used to continuously trap cells in the standing wave, thereby causing the cells to agglomerate, aggregate, clump, or coalesce together, and subsequently settle out of the fluid due to enhanced gravitational forces or rise out of the fluid due to enhanced buoyancy. This lateral ARF can also be used to retain cells in a bioreactor while the bioreactor process continues, which is especially true for a perfusion bioreactor. Additionally, as explained above, this action of the acoustic forces (i.e., lateral and axial acoustic forces) on the trapped particles results in formation of tightly packed clusters through concentration, agglomeration and/or coalescence of particles that settle through enhanced gravity (particles heavier than the host fluid) or buoyancy (particles lighter than the host fluid). Relatively large solids of one material can thus be separated from smaller particles of a different material, the same material, and/or the host fluid through enhanced gravitational separation. Additionally, the action of the acoustic forces on the trapped cells results in formation of tightly packed clusters.

The devices using multi-dimensional acoustic standing waves as disclosed herein are capable of achieving concentration of at least 100 times the original cell concentration, including from about 150 times to about 300 times the original cell concentration, and up to about 600 times the original cell concentration. Put another way, the original feed volume of a mixture of host fluid and biological cells can be reduced by a volume concentration factor of from about 150 to about 600. Such concentration increases the efficiency of subsequent downstream filtration/processing stages.

The multi-dimensional standing wave generates acoustic radiation forces in both the axial direction (i.e., in the direction of the standing wave, between the transducer and the reflector, perpendicular to the flow direction) and the lateral direction (i.e., in the flow direction). As the mixture flows through the flow chamber, particles in suspension experience a strong axial force component in the direction of the standing wave. Since this acoustic force is perpendicular to the flow direction and the drag force, it quickly moves the particles to pressure nodal planes or anti-nodal planes, depending on the contrast factor of the particle. The lateral acoustic radiation force then acts to move the concentrated particles towards the center of each planar node, resulting in agglomeration or clumping. The lateral acoustic radiation force component can overcome fluid drag for such clumps of particles to continually grow and then drop out of the mixture due to gravity. Therefore, both the drop in drag per particle as the particle cluster increases in size, as well as the drop in acoustic radiation force per particle as the particle cluster grows in size, may be considered in determining the effectiveness of the acoustic separator device. In the present disclosure, the lateral force component and the axial force component of the multi-dimensional acoustic standing wave are of the same order of magnitude. In this regard, it is noted that in a multi-dimensional acoustic standing wave, the axial force is stronger than the lateral force, but the lateral force of a multi-dimensional acoustic standing wave is much higher than the lateral force of a planar standing wave, usually by two orders of magnitude or more.

Figure 2:
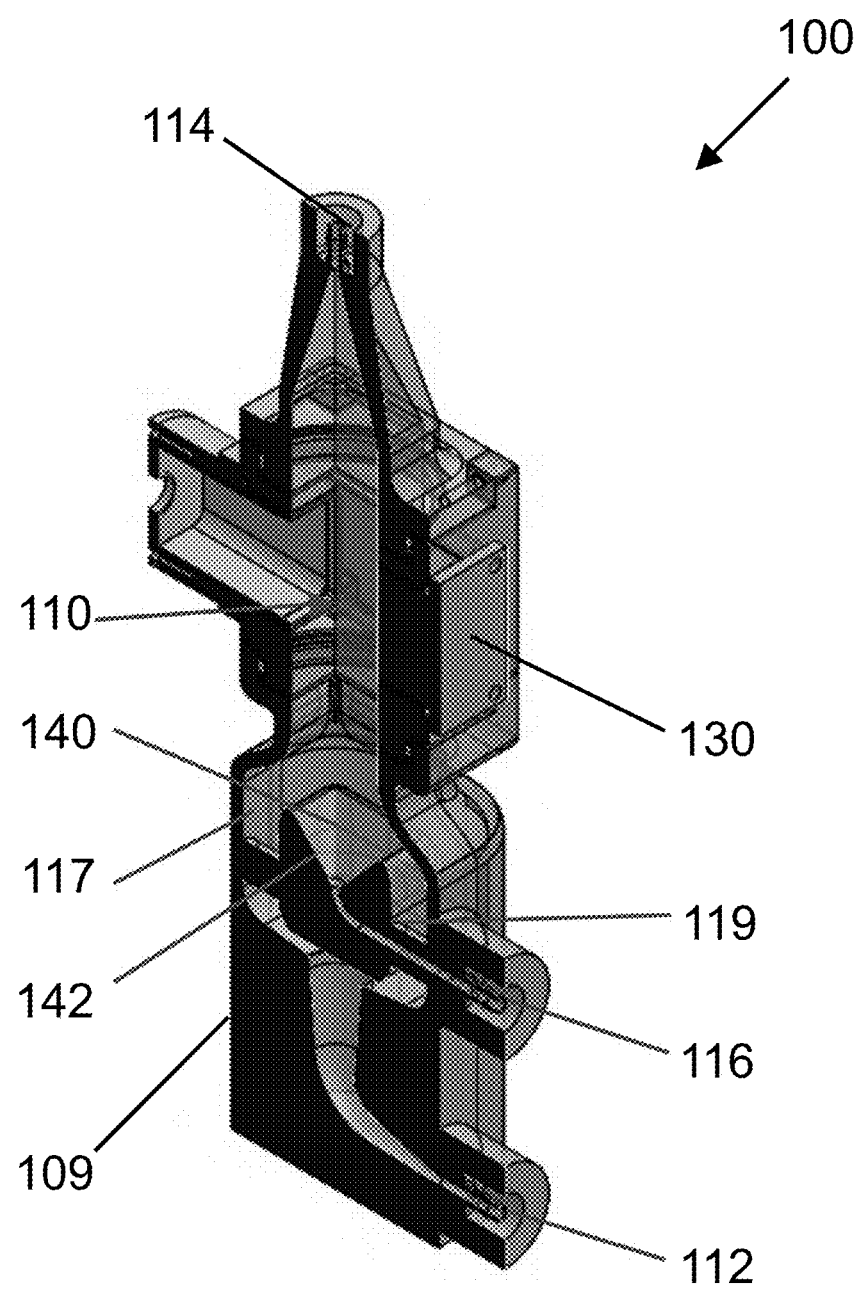
FIG. 2 is a cross-sectional illustration of the acoustophoretic device of FIG. 1.

With reference now to FIG. 1 and FIG. 2, a first exemplary embodiment of an acoustophoretic device 100 for concentrating target cells having an original cell concentration in a host fluid is depicted. The acoustophoretic device 100 includes a flow chamber 110 having at least one inlet and at least one outlet. In the embodiment depicted in FIG. 1 and FIG. 2, the flow chamber 110 includes inlet 112, permeate outlet 114, concentrate outlet 116, an ultrasonic transducer 120, and a reflector 130.

The flow chamber 110 is the region of the device 100 through which is flowed an initial mixture of a host fluid and the biological cells. In the embodiment shown in FIG. 1 and FIG. 2, the flow chamber 110 is defined by inlet 112, permeate outlet 114, and concentrate outlet 116. As can be seen in FIG. 1 and FIG. 2, the flow chamber 110 is further defined by a sidewall 115 to which the ultrasonic transducer 120 and the reflector 130 are coupled. As seen here, the sidewall is shaped so that the ultrasonic transducer and reflector are located on opposite sides thereof.

Inlet 112 is located at a first end 106 of the flow chamber 110. In particular embodiments, the ingress of fluid through the inlet 112 can be configured to occur toward the bottom end of the inlet 112, such that the inflow of fluid into the flow chamber 110 occurs closer to the bottom end of the flow chamber 110 than the top end thereof.

As depicted in FIG. 1 and FIG. 2, the inlet 112 is located along a first side 107 of the device 100. In FIG. 1 and FIG.

2, the first side 107 of the device also houses the reflector 130, while a second side 109 of the device, opposite the first side thereof, houses the ultrasonic transducer 120. It is, however, contemplated that the inlet 112 could be located along the second side 109 of the device (i.e., on the same side as the ultrasonic transducer) or on another side of the device.

In the embodiment depicted in FIG. 1, the permeate outlet 114 is located at a second end 108 of the flow chamber 100. The permeate outlet 114 is generally used to recover the host fluid and residual biological cells from the flow chamber 110. In comparison, the concentrate outlet 116 is located between the inlet 112 and the permeate outlet 114, below the ultrasonic transducer 120 and the reflector 130. The concentrate outlet 116 is generally configured to recover biological cells from the flow chamber 110. In this regard, the permeate outlet 114 is generally located above the ultrasonic transducer 120 and the reflector 130, while and the concentrate outlet 116 is generally located below the ultrasonic transducer 120 and the reflector 130.

In the embodiment depicted in FIG. 1 and FIG. 2, the device 100 is vertically oriented, such that the first end 106 of the device is the bottom end thereof and the second end 108 of the device is the top end thereof. In this way, the mixture of the host fluid and the biological cells flows vertically upwards through the flow chamber from the one inlet 112 toward the permeate outlet 114.

As can be best seen in FIG. 2, the device 100 also includes a collector 140. The collector 140 is located in the flow chamber 110 between the inlet 112 and the ultrasonic transducer 120 and the reflector 130. The collector 140 is located above the concentrate outlet 116 and, in particular, is defined by angled walls 142 that lead to the concentrate outlet 116. Put another way, the collector 140 leads into a common well defined by angled walls 142 that taper downwards in cross-sectional area (i.e. larger area to smaller area) to a vertex at the bottom of the collector, which is fluidically connected to and drains off one side into the concentrate outlet 116 via flowpath 119. In this way, the multi-dimensional acoustic standing wave can direct the concentrated biological cells to the collector 140 for collection and removal from the flow chamber 110 via the concentrate outlet 116. An annular plenum 117 surrounds the collector 140, permitting the mixture of host fluid/cells to flow from the inlet 112 around the collector 140 into the flow chamber 110.

As seen here, preferably, fluid flows through the device upwards. The mixture of host fluid containing target cells enters the apparatus through inlet 112 at a bottom end of the device. The fluid mixture then makes a sharp turn to flow upwards. This change in direction desirably reduces turbulence, producing near plug flow upwards through the device. The fluid mixture flows upwards through the annular plenum 117 and up into the flow chamber 110. There, the fluid mixture encounters the multi-dimensional acoustic standing waves, which are used to separate the target cells from the host fluid. Agglomeration, aggregation, clumping, or coalescence of the target cells occurs within the acoustic standing waves, which also concentrates the target cells. Host fluid, containing residual cells and other materials not separated out, then exits through permeate/flow outlet 114.

As the target cells are concentrated, they eventually overcome the combined effect of the fluid flow drag forces and acoustic radiation force, and they fall downwards into collector 140. They can then be flowed through flowpath 119 and collected at concentrate outlet 116. A much higher number of cells is obtained in a smaller volume, i.e. the target cells are concentrated.

Figure 3:
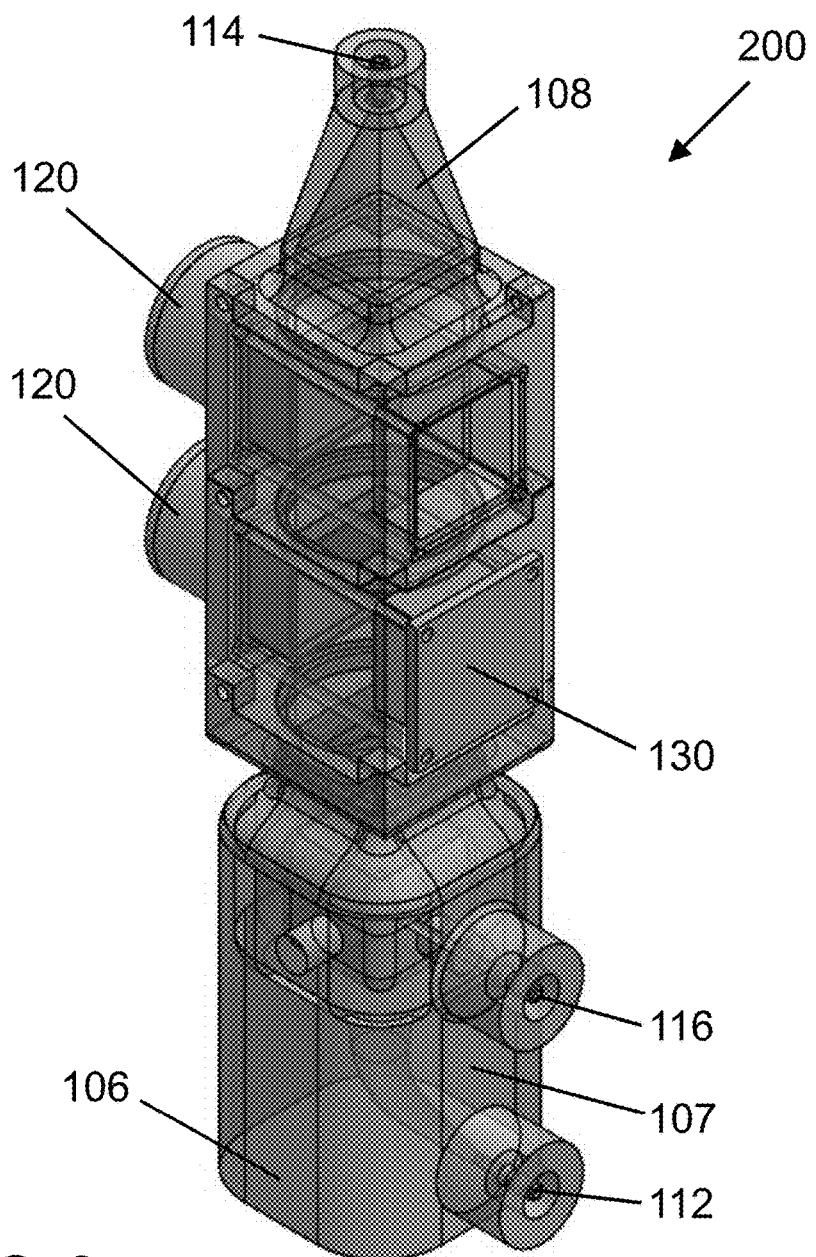
FIG. 3 is a perspective view of another exemplary acoustophoretic device according to the present disclosure.
Figure 4:
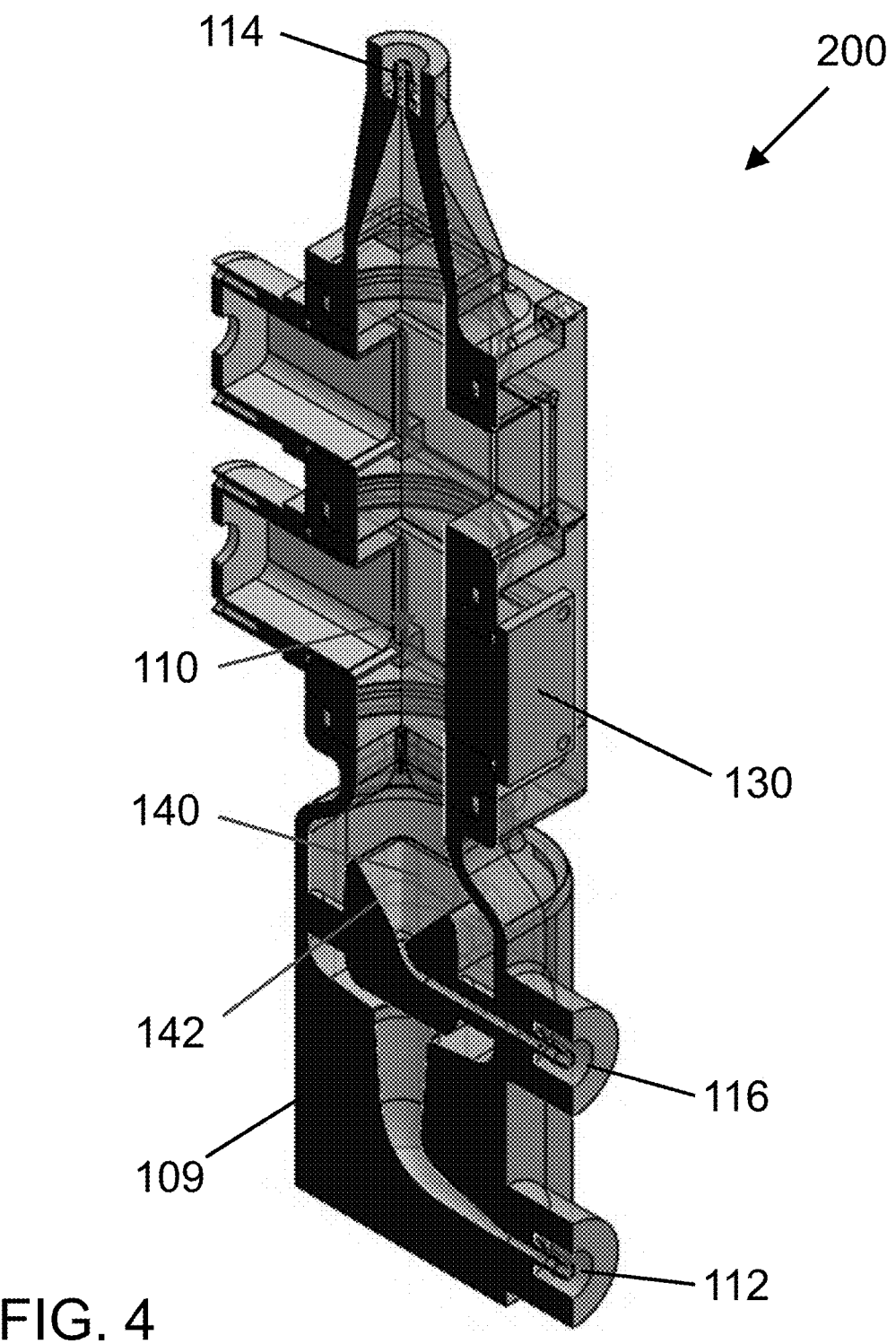
FIG. 4 is a cross-sectional illustration of the acoustophoretic device of FIG. 3.

Turning now to FIG. 3 and FIG. 4, another exemplary embodiment of an acoustophoretic device 200 is depicted. The acoustophoretic device 200 of FIG. 3 and FIG. 4 is very similar to the acoustophoretic device 100 of FIG. 1 and FIG. 2. However, the acoustophoretic device 200 depicted in FIG. 3 and FIG. 4 includes a plurality of ultrasonic transducers 120. As shown here, the ultrasonic transducers 120 are serially arranged between the concentrate outlet 116 and the permeate outlet 114, and downstream of the inlet 112. The frequency/power of the multi-dimensional acoustic standing wave(s) generated by each individual ultrasonic transducer of the device may be varied to capture cells of different sizes, or they may be operated at the same frequency so that the downstream ultrasonic transducer(s) capture additional target cells that were not captured by an upstream ultrasonic transducer. This feature permits recovery of the cells and/or the clarified fluid, as desired.

Prior to discussing further optimization of the devices, it is helpful to provide an explanation now of how multi-dimensional acoustic standing waves are generated. The multi-dimensional acoustic standing wave needed for particle collection is obtained by driving an ultrasonic transducer at a frequency that both generates the acoustic standing wave and excites a fundamental 3D vibration mode of the transducer crystal. Perturbation of the piezoelectric crystal in an ultrasonic transducer in a multimode fashion allows for generation of a multidimensional acoustic standing wave. A piezoelectric crystal can be specifically designed to deform in a multimode fashion at designed frequencies, allowing for generation of a multi-dimensional acoustic standing wave. The multi-dimensional acoustic standing wave may be generated by distinct modes of the piezoelectric crystal such as a 3×3 mode that would generate multi-dimensional acoustic standing waves. A multitude of multidimensional acoustic standing waves may also be generated by allowing the piezoelectric crystal to vibrate through many different mode shapes. Thus, the crystal would excite multiple modes such as a 0×0 mode (i.e. a piston mode) to a 1×1, 2×2, 1×3, 3×1, 3×3, and other higher order modes and then cycle back through the lower modes of the crystal (not necessarily in straight order). This switching or dithering of the crystal between modes allows for various multidimensional wave shapes, along with a single piston mode shape to be generated over a designated time.

Some further explanation of the ultrasonic transducers used in the devices, systems, and methods of the present disclosure may be helpful as well. In this regard, the transducers use a piezoelectric crystal, usually made of PZT-8 (lead zirconate titanate). Such crystals may have a 1 inch diameter and a nominal 2 MHz resonance frequency, and may also be of a larger size. Each ultrasonic transducer module can have only one crystal, or can have multiple crystals that each act as a separate ultrasonic transducer and are either controlled by one or multiple amplifiers. The crystals can be square, rectangular, irregular polygon, or generally of any arbitrary shape. The transducer(s) is/are used to create a pressure field that generates forces of the same order of magnitude both orthogonal to the standing wave direction (lateral) and in the standing wave direction (axial).

Figure 20:
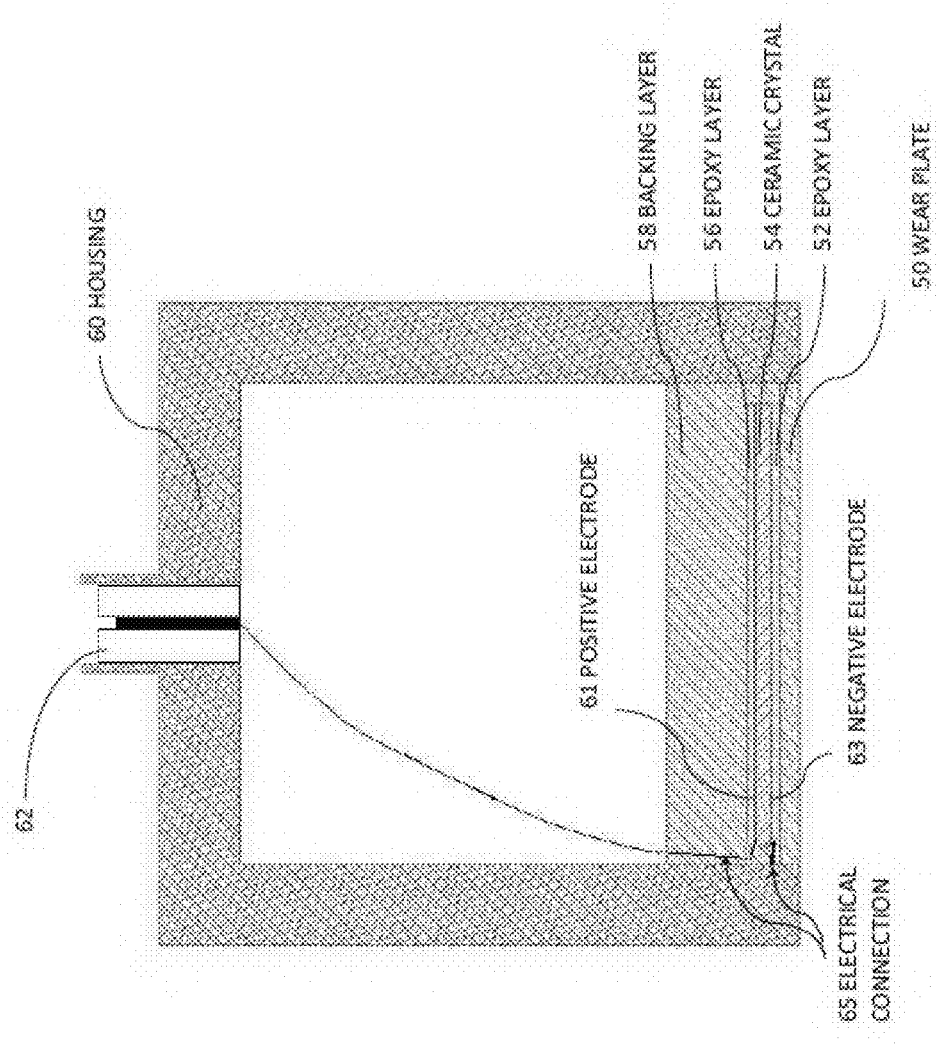
FIG. 20 is a cross-sectional diagram of a conventional ultrasonic transducer.

FIG. 20 is a cross-sectional diagram of a conventional ultrasonic transducer. This transducer has a wear plate 50 at a bottom end, epoxy layer 52, ceramic crystal 54 (made of, e.g. PZT), an epoxy layer 56, and a backing layer 58. On either side of the ceramic crystal, there is an electrode: a positive electrode 61 and a negative electrode 63. The epoxy layer 56 attaches backing layer 58 to the crystal 54. The entire assembly is contained in a housing 60 which may be made out of, for example, aluminum. An electrical adapter 62 provides connection for wires to pass through the housing and connect to leads (not shown) which attach to the crystal 54. Typically, backing layers are designed to add damping and to create a broadband transducer with uniform displacement across a wide range of frequency and are designed to suppress excitation at particular vibrational eigen-modes. Wear plates are usually designed as impedance transformers to better match the characteristic impedance of the medium into which the transducer radiates.

Figure 21:
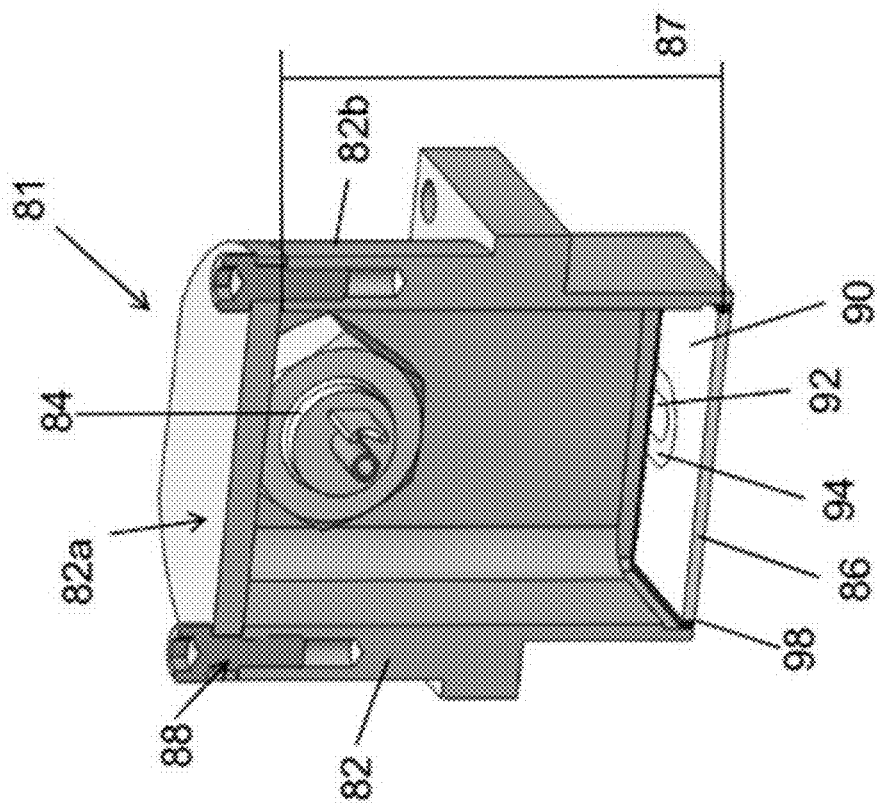
FIG. 21 is a cross-sectional diagram of an ultrasonic transducer of the present disclosure. An air gap is present within the transducer, and no backing layer or wear plate is present.

FIG. 21 is a cross-sectional view of an ultrasonic transducer 81 of the present disclosure. Transducer 81 is shaped as a disc or a plate, and has an aluminum housing 82. The piezoelectric crystal is a mass of perovskite ceramic crystals, each consisting of a small, tetravalent metal ion, usually titanium or zirconium, in a lattice of larger, divalent metal ions, usually lead or barium, and O2− ions. As an example, a PZT (lead zirconate titanate) crystal 86 defines the bottom end of the transducer, and is exposed from the exterior of the housing. The crystal has an interior surface and an exterior surface. The crystal is supported on its perimeter by a small elastic layer 98, e.g. silicone or similar material, located between the crystal and the housing. Put another way, no wear layer is present. In particular embodiments, the crystal is an irregular polygon, and in further embodiments is an asymmetrical irregular polygon.

Figure 22:
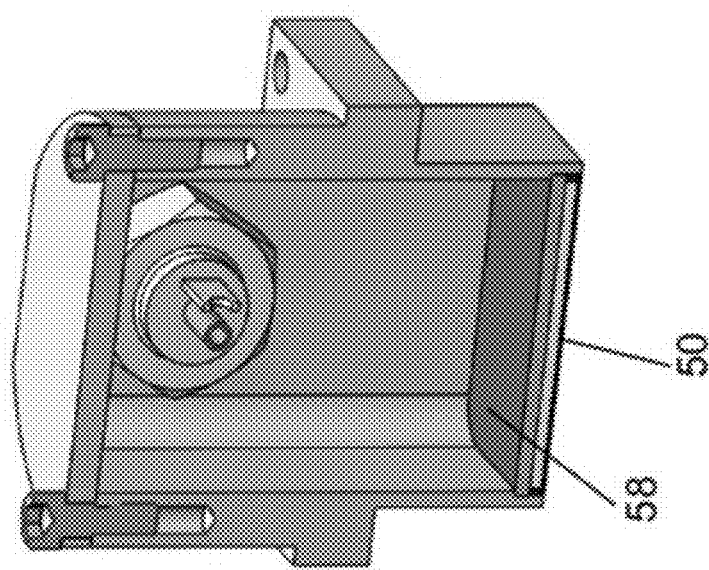
FIG. 22 is a cross-sectional diagram of an ultrasonic transducer of the present disclosure. An air gap is present within the transducer, and a backing layer and wear plate are present.

Screws 88 attach an aluminum top plate 82a of the housing to the body 82b of the housing via threads. The top plate includes a connector 84 for powering the transducer. The top surface of the PZT crystal 86 is connected to a positive electrode 90 and a negative electrode 92, which are separated by an insulating material 94. The electrodes can be made from any conductive material, such as silver or nickel. Electrical power is provided to the PZT crystal 86 through the electrodes on the crystal. Note that the crystal 86 has no backing layer or epoxy layer. Put another way, there is an air gap 87 in the transducer between aluminum top plate 82a and the crystal 86 (i.e. the air gap is completely empty). A minimal backing 58 (on the interior surface) and/or wear plate 50 (on the exterior surface) may be provided in some embodiments, as seen in FIG. 22.

The transducer design can affect performance of the system. A typical transducer is a layered structure with the ceramic crystal bonded to a backing layer and a wear plate. Because the transducer is loaded with the high mechanical impedance presented by the standing wave, the traditional design guidelines for wear plates, e.g., half wavelength thickness for standing wave applications or quarter wavelength thickness for radiation applications, and manufacturing methods may not be appropriate. Rather, in one embodiment of the present disclosure the transducers, there is no wear plate or backing, allowing the crystal to vibrate in one of its eigenmodes (i.e. near eigenfrequency) with a high Q-factor. The vibrating ceramic crystal/disk is directly exposed to the fluid flowing through the flow chamber.

Removing the backing (e.g. making the crystal air backed) also permits the ceramic crystal to vibrate at higher order modes of vibration with little damping (e.g. higher order modal displacement). In a transducer having a crystal with a backing, the crystal vibrates with a more uniform displacement, like a piston. Removing the backing allows the crystal to vibrate in a non-uniform displacement mode. The higher order the mode shape of the crystal, the more nodal lines the crystal has. The higher order modal displacement of the crystal creates more trapping lines, although the correlation of trapping line to node is not necessarily one to one, and driving the crystal at a higher frequency will not necessarily produce more trapping lines.

In some embodiments, the crystal may have a backing that minimally affects the Q-factor of the crystal (e.g. less than 5%). The backing may be made of a substantially acoustically transparent material such as balsa wood, foam, or cork which allows the crystal to vibrate in a higher order mode shape and maintains a high Q-factor while still providing some mechanical support for the crystal. The backing layer may be a solid, or may be a lattice having holes through the layer, such that the lattice follows the nodes of the vibrating crystal in a particular higher order vibration mode, providing support at node locations while allowing the rest of the crystal to vibrate freely. The goal of the lattice work or acoustically transparent material is to provide support without lowering the Q-factor of the crystal or interfering with the excitation of a particular mode shape.

Placing the crystal in direct contact with the fluid also contributes to the high Q-factor by avoiding the dampening and energy absorption effects of the epoxy layer and the wear plate. Other embodiments may have wear plates or a wear surface to prevent the PZT, which contains lead, contacting the host fluid. This separation of the transducer from the host fluid may be desirable in, for example, biological applications such as separating blood. Such applications might use a wear layer such as chrome, electrolytic nickel, or electroless nickel. Chemical vapor deposition could also be used to apply a layer of poly(p-xylylene) (e.g. Parylene) or other polymers or polymer films. Organic and biocompatible coatings such as silicone or polyurethane are also usable as a wear surface.

Figure 23:
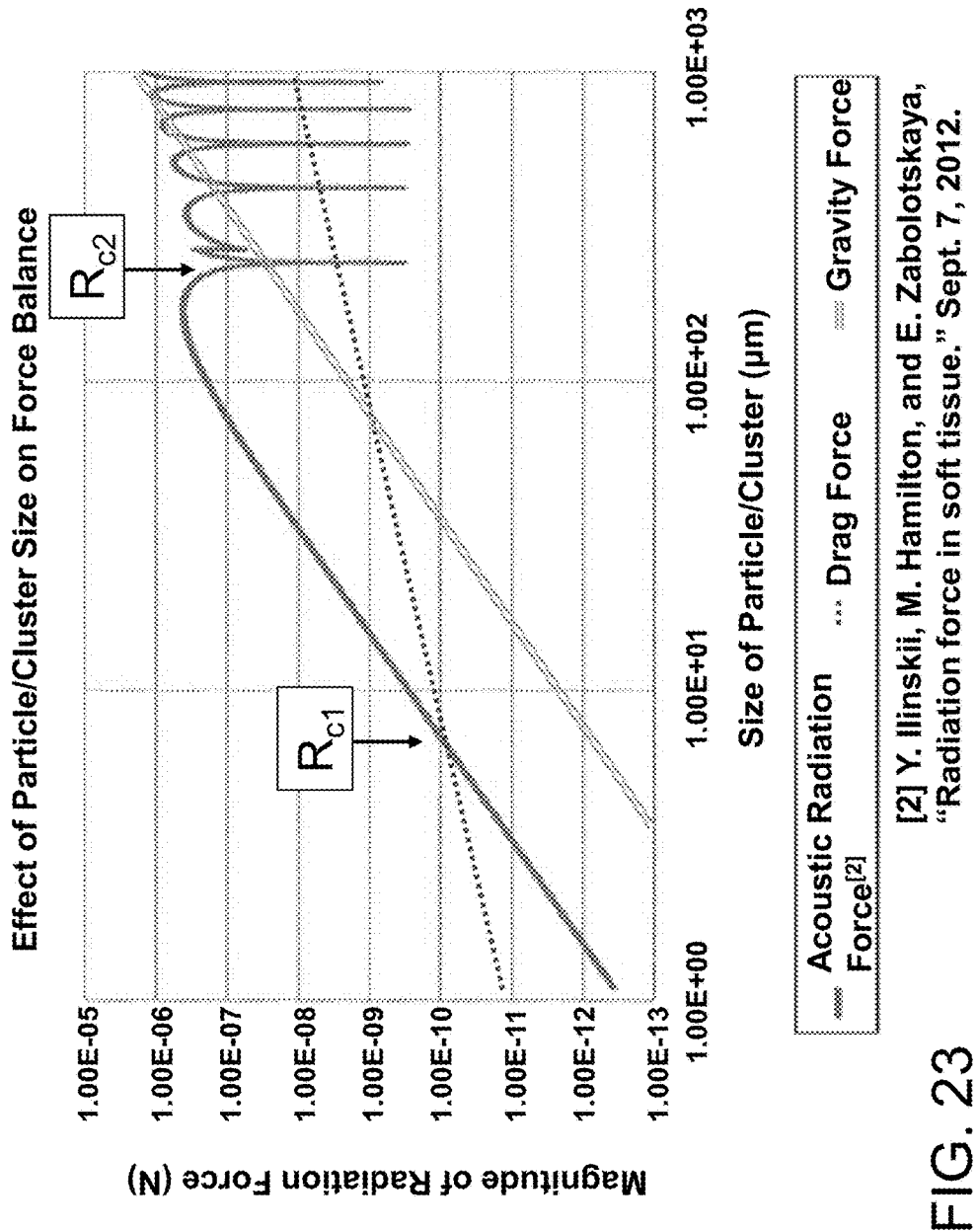
FIG. 23 is a graph showing the relationship of the acoustic radiation force, gravity/buoyancy force, and Stokes' drag force to particle size. The horizontal axis is in microns (μm) and the vertical axis is in Newtons (N).

FIG. 23 is a log-log graph (logarithmic y-axis, logarithmic x-axis) that shows the scaling of the acoustic radiation force, fluid drag force, and buoyancy force with particle radius, and provides an explanation for the separation of particles using acoustic radiation forces. The buoyancy force is a particle volume dependent force, and is therefore negligible for particle sizes on the order of micron, but grows, and becomes significant for particle sizes on the order of hundreds of microns. The fluid drag force (Stokes drag force) scales linearly with fluid velocity, and therefore typically exceeds the buoyancy force for micron sized particles, but is negligible for larger sized particles on the order of hundreds of microns. The acoustic radiation force scaling is different. When the particle size is small, Gor'kov's equation is accurate and the acoustic trapping force scales with the volume of the particle. Eventually, when the particle size grows, the acoustic radiation force no longer increases with the cube of the particle radius, and will rapidly vanish at a certain critical particle size. For further increases of particle size, the radiation force increases again in magnitude but with opposite phase (not shown in the graph). This pattern repeats for increasing particle sizes.

Initially, when a suspension is flowing through the system with primarily small micron sized particles, the acoustic radiation force may balance the combined effect of fluid drag force and buoyancy force to permit a particle to be trapped in the standing wave. In FIG. 23, this happens at a particle size labeled as $R_{c1}$. The graph then indicates that all larger particles will be trapped as well. Therefore, when small particles are trapped in the standing wave, particles coalescence/clumping/aggregation/agglomeration takes place, resulting in continuous growth of effective particle size. As particles cluster, the total drag on the cluster is much lower than the sum of the drag forces on the individual particles. In essence, as the particles cluster, they shield each other from the fluid flow and reduce the overall drag of the cluster. As the particle cluster size grows, the acoustic radiation force reflects off the cluster, such that the net acoustic radiation force decreases per unit volume. The acoustic lateral forces on the particles may be greater than the drag forces to permit the clusters to remain stationary and grow in size.

Particle size growth continues until the buoyancy force becomes dominant, which is indicated by a second critical particle size, $R_{c2}$. The buoyancy force per unit volume of the cluster remains constant with cluster size, since it is a function of the particle density, cluster concentration and gravity constant. Therefore, as the cluster size increases, the buoyancy force on the cluster increases faster than the acoustic radiation force. At the size $R_{c2}$, the particles will rise or sink, depending on their relative density with respect to the host fluid. At this size, acoustic forces are secondary, gravity/buoyancy forces become dominant, and the particles naturally drop out or rise out of the host fluid. Not all particles will drop out, and those remaining particles and new particles entering the flow chamber will continue to move to the three-dimensional nodal locations, repeating the growth and drop-out process. This phenomenon explains the quick drops and rises in the acoustic radiation force beyond size $R_{c2}$. Thus, FIG. 23 explains how small particles can be trapped continuously in a standing wave, grow into larger particles or clumps, and then eventually will rise or settle out because of increased buoyancy force.

The size, shape, and thickness of the transducer determine the transducer displacement at different frequencies of excitation, which in turn affects particle separation efficiency. Higher order modal displacements generate three-dimensional acoustic standing waves with strong gradients in the acoustic field in all directions, thereby creating equally strong acoustic radiation forces in all directions, leading to multiple trapping lines, where the number of trapping lines correlate with the particular mode shape of the transducer.

Figure 24:
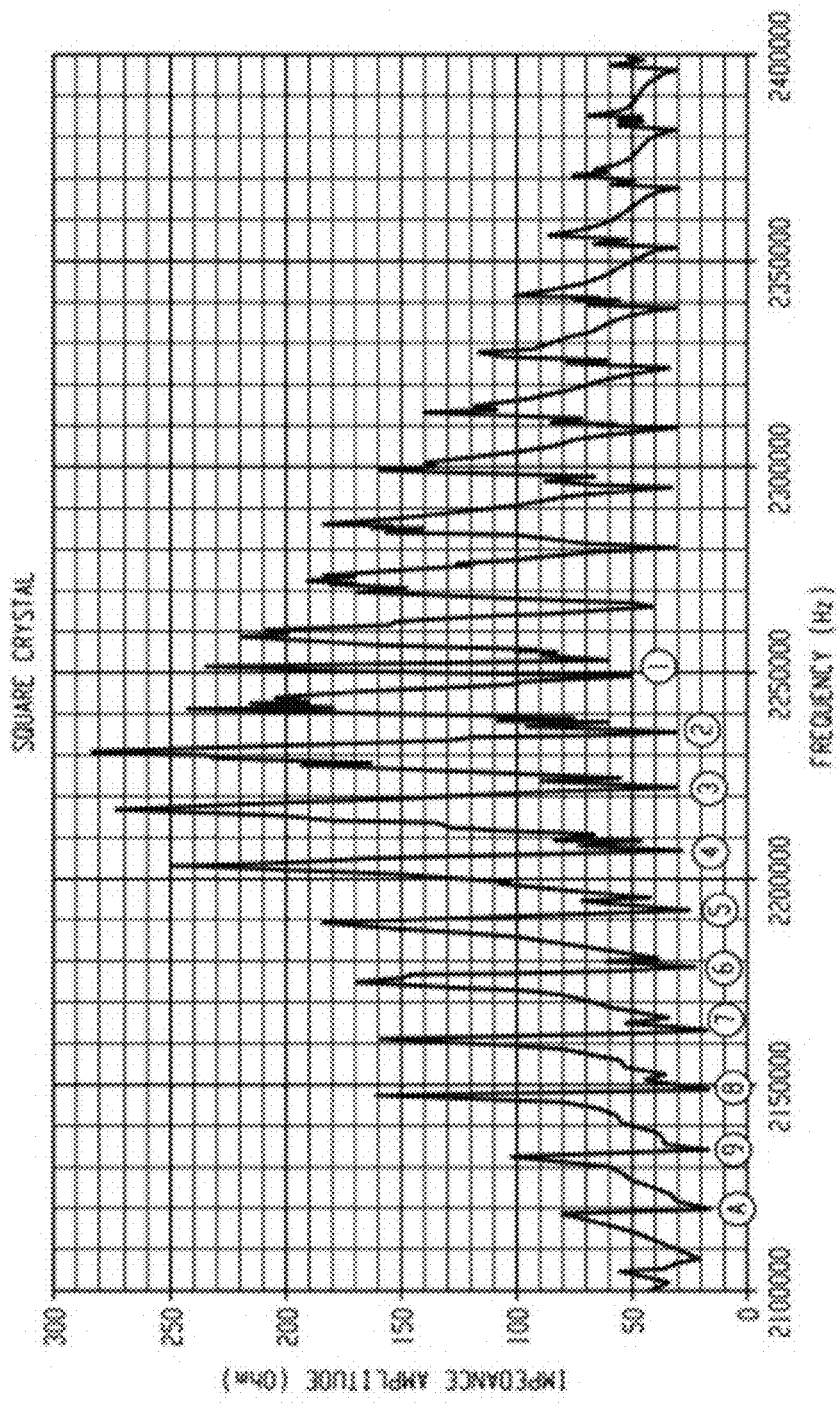
FIG. 24 is a graph of electrical impedance amplitude versus frequency for a square transducer driven at different frequencies.

FIG. 24 shows the measured electrical impedance amplitude of the transducer as a function of frequency in the vicinity of the 2.2 MHz transducer resonance. The minima in the transducer electrical impedance correspond to acoustic resonances of a water column and represent potential frequencies for operation. Numerical modeling has indicated that the transducer displacement profile varies significantly at these acoustic resonance frequencies, and thereby directly affects the acoustic standing wave and resulting trapping force. Since the transducer operates near its thickness resonance, the displacements of the electrode surfaces are essentially out of phase. The typical displacement of the transducer electrodes is not uniform and varies depending on frequency of excitation. Higher order transducer displacement patterns result in higher trapping forces and multiple stable trapping lines for the captured particles.

To investigate the effect of the transducer displacement profile on acoustic trapping force and particle separation efficiencies, an experiment was repeated ten times, with all conditions identical except for the excitation frequency. Ten consecutive acoustic resonance frequencies, indicated by circled numbers 1-9 and letter A on FIG. 24, were used as excitation frequencies. The conditions were experiment duration of 30 min, a 1000 ppm oil concentration of approximately 5-micron SAE-30 oil droplets, a flow rate of 500 ml/min, and an applied power of 20 W.

As the emulsion passed by the transducer, the trapping lines of oil droplets were observed and characterized. The characterization involved the observation and pattern of the number of trapping lines across the fluid channel, as shown in FIG. 25A, for seven of the ten resonance frequencies identified in FIG. 24.

FIG. 25B shows an isometric view of the device in which the trapping line locations are being determined. FIG. 25C is a view of the device as it appears when looking down the inlet, along arrow 251. FIG. 25D is a view of the device as it appears when looking directly at the transducer face, along arrow 253.

The effect of excitation frequency clearly determines the number of trapping lines, which vary from a single trapping line at the excitation frequency of acoustic resonance 5 and 9, to nine trapping lines for acoustic resonance frequency 4. At other excitation frequencies four or five trapping lines are observed. Different displacement profiles of the transducer can produce different (more) trapping lines in the standing waves, with more gradients in displacement profile generally creating higher trapping forces and more trapping lines. It is noted that although the different trapping line profiles shown in FIG. 25A were obtained at the frequencies shown in FIG. 24, these trapping line profiles can also be obtained at different frequencies.

FIG. 25A shows the different crystal vibration modes possible by driving the crystal to vibrate at different fundamental frequencies of vibration. The 3D mode of vibration of the crystal is carried by the acoustic standing wave across the fluid in the chamber all the way to the reflector and back. The resulting multi-dimensional standing wave can be thought of as containing two components. The first component is a planar out-of-plane motion component (uniform displacement across crystal surface) of the crystal that generates a standing wave, and the second component is a displacement amplitude variation with peaks and valleys occurring in both lateral directions of the crystal surface. Three-dimensional force gradients are generated by the standing wave. These three-dimensional force gradients result in lateral radiation forces that stop and trap the particles with respect to the flow by overcoming the viscous drag force. In addition, the lateral radiation forces are responsible for creating tightly packed clusters of particles. Therefore, particle separation and gravity-driven collection depends on generating a multi-dimensional standing wave that can overcome the particle drag force as the mixture flows through the acoustic standing wave. Multiple particle clusters are formed along trapping lines in the axial direction of the standing wave, as presented schematically in FIG. 25A.

One specific application for the acoustophoresis devices disclosed herein is in the processing of bioreactor materials. It is important to be able to filter all of the cells and cell debris from the expressed materials that are in the fluid stream. The expressed materials are composed of biomolecules such as recombinant proteins or monoclonal antibodies, and such biomolecules or the cells themselves are the desired product to be recovered. Through the use of acoustophoresis, separation is very efficient and leads to very little loss. This efficiency is an improvement over current filtration processes (depth filtration, tangential flow filtration, and the like), which show limited efficiencies at high cell densities, with losses in the filter beds themselves of up to 5% of the materials produced by the bioreactor. The use of mammalian cell cultures including Chinese hamster ovary (CHO), NSO hybridoma cells, baby hamster kidney (BHK) cells, T cells, B cells, NK cells, and human cells has proven to be a very efficacious way of producing/expressing the recombinant proteins and monoclonal antibodies demanded of today's pharmaceuticals.

It is contemplated that the acoustophoretic devices of the present disclosure can be used in a filter "train," in which multiple different filtration steps are used to clarify or purify an initial fluid/particle mixture to obtain the desired product and manage different materials from each filtration step. Each filtration step can be optimized to remove a particular material, improving the overall efficiency of the clarification process. An individual acoustophoretic device can operate as one or multiple filtration steps. For example, each individual ultrasonic transducer within a particular acoustophoretic device can to operated to trap materials within a given particle range. It is particularly contemplated that the acoustophoretic device can be used to remove large quantities of material, reducing the burden on subsequent downstream filtration steps/stages. However, it is contemplated that additional filtration steps/stages can be placed upstream or downstream of the acoustophoretic device. Of course, multiple acoustophoretic devices can be used as well. It is particularly contemplated that desirable biomolecules or cells can be recovered/separated after such filtration/purification.

The outlets of the acoustophoretic devices of the present disclosure (e.g. clarified fluid and concentrated cells) can be fluidly connected to any other filtration step or filtration stage. Such filtration steps can include various methods such as depth filtration, sterile filtration, size exclusion filtration, or tangential filtration. Depth filtration uses physical porous filtration mediums that can retain material through the entire depth of the filter. In sterile filtration, membrane filters with extremely small pore sizes are used to remove microorganisms and viruses, generally without heat or irradiation or exposure to chemicals. Size exclusion filtration separates materials by size and/or molecular weight using physical filters with pores of given size. In tangential filtration, the majority of fluid flow is across the surface of the filter, rather than into the filter.

Chromatography can also be used, including cationic chromatography columns, anionic chromatography columns, affinity chromatography columns, mixed bed chromatography columns. Other hydrophilic/hydrophobic processes can also be used for filtration purposes.

The following examples are provided to illustrate the devices and methods of the present disclosure. The examples are merely illustrative and are not intended to limit the disclosure to the materials, conditions, or process parameters set forth therein.

EXAMPLES

In FIGS. 5-19, various studies were performed using device 100. In each of the studies, the mixture was a mixture of yeast cells and a host fluid, which serves as a good simulant for the concentration of biological cells.

Figure 5:
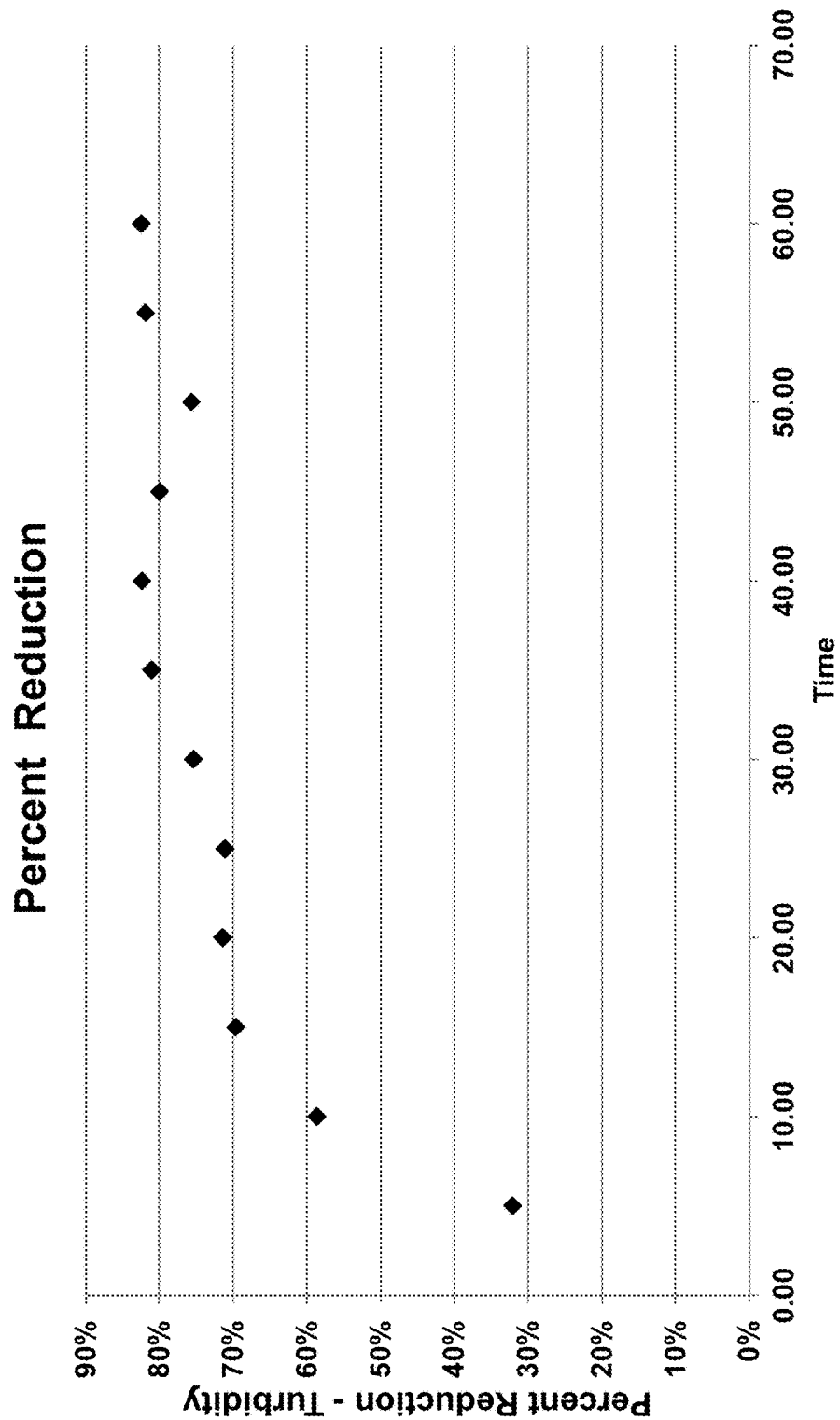
FIG. 5 is a graph showing the performance of an acoustophoretic device such as that illustrated in FIG. 1, at a frequency of 2.182 megahertz (MHz) and a flow rate of 15 mL/min. The graph has a y-axis of percent reduction, and runs from 0% to 90% in intervals of 10%. The x-axis is test duration in minutes, and runs from 0 to 70 in intervals of 10.
Figure 6:
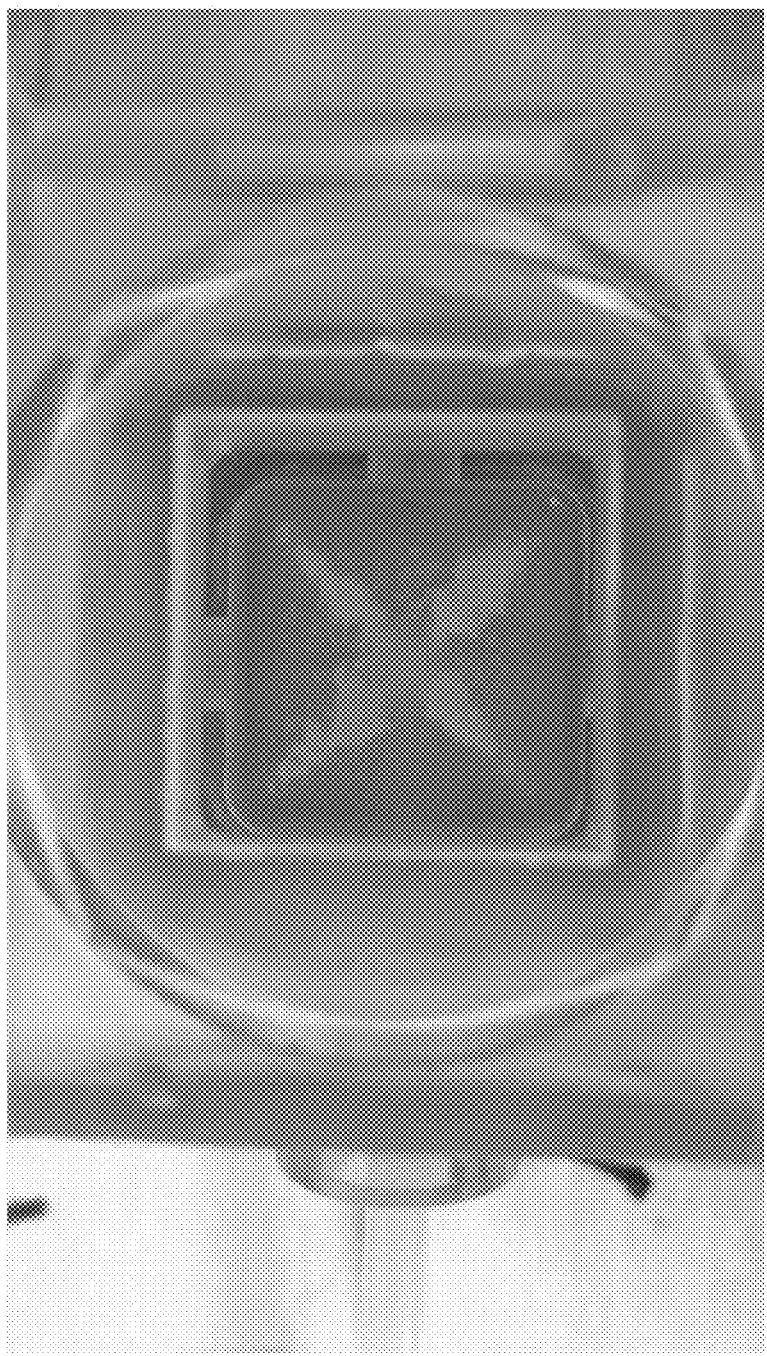
FIG. 6 is a photograph taken during the experiment of FIG. 5.

For the study depicted in FIG. 5, a mixture having a TCD (total cell density) of $1.52 \times 10^6$ cells/mL and TCC (total cell count) of $1.37 \times 10^9$ cells was used. In total, three tests were run with 900 mL of mixture flowed through the device at a flow rate of 15 mL/minute and the ultrasonic transducer operated at a starting frequency of 2.182 MHz. For each test, the turbidity was measured in NTU (Nephelometric Turbidity Units) from the beginning of the test (time=0) to the end of the test (time=60 minutes) at intervals of five minutes. After testing, 900 mL of permeate (i.e., the host fluid and residual yeast cells) was recovered and had a TCD of $1.60 \times 10^5$ cells/mL and a TCC of $1.44 \times 10^8$ cells. For the concentrate (i.e., the recovered yeast cells), 4 mL was recovered and had a TCD of $1.45 \times 10^8$ cells/mL and a TCC of $5.79 \times 10^8$ cells. FIG. 6 is a photograph of the yeast cells being concentrated in the flow chamber. When the three tests were averaged together, the device was shown to exhibit a volume concentration factor (i.e., the feed volume divided by the concentrate volume) of 225, a cell retention rate of 42%, and a cell density reduction of 89%. The turbidity reduction performance of the device is summarized in the table below.

| Time | Test 1 NTU | Test 2 NTU | Test 3 NTU | Average | Reduction (%) |
|---|---|---|---|---|---|
| 0 | 19.9 | | | 19.90 | |
| 5 | 14.14 | 13.44 | 12.94 | 13.51 | 32 |
| 10 | 8.22 | 8.2 | 8.24 | 8.22 | 59 |
| 15 | 6.13 | 5.92 | 6.04 | 6.03 | 70 |
| 20 | 5.73 | 5.67 | 5.66 | 5.69 | 71 |
| 25 | 5.81 | 5.71 | 5.72 | 5.75 | 71 |
| 30 | 4.95 | 4.94 | 4.8 | 4.90 | 75 |
| 35 | 3.83 | 3.77 | 3.73 | 3.78 | 81 |
| 40 | 3.52 | 3.57 | 3.43 | 3.51 | 82 |
| 45 | 4.01 | 4 | 3.95 | 3.99 | 80 |
| 50 | 4.83 | 4.9 | 4.8 | 4.84 | 76 |
| 55 | 3.68 | 3.61 | 3.53 | 3.61 | 82 |
| 60 | 3.52 | 3.48 | 3.49 | 3.50 | 82 |

Figure 7:
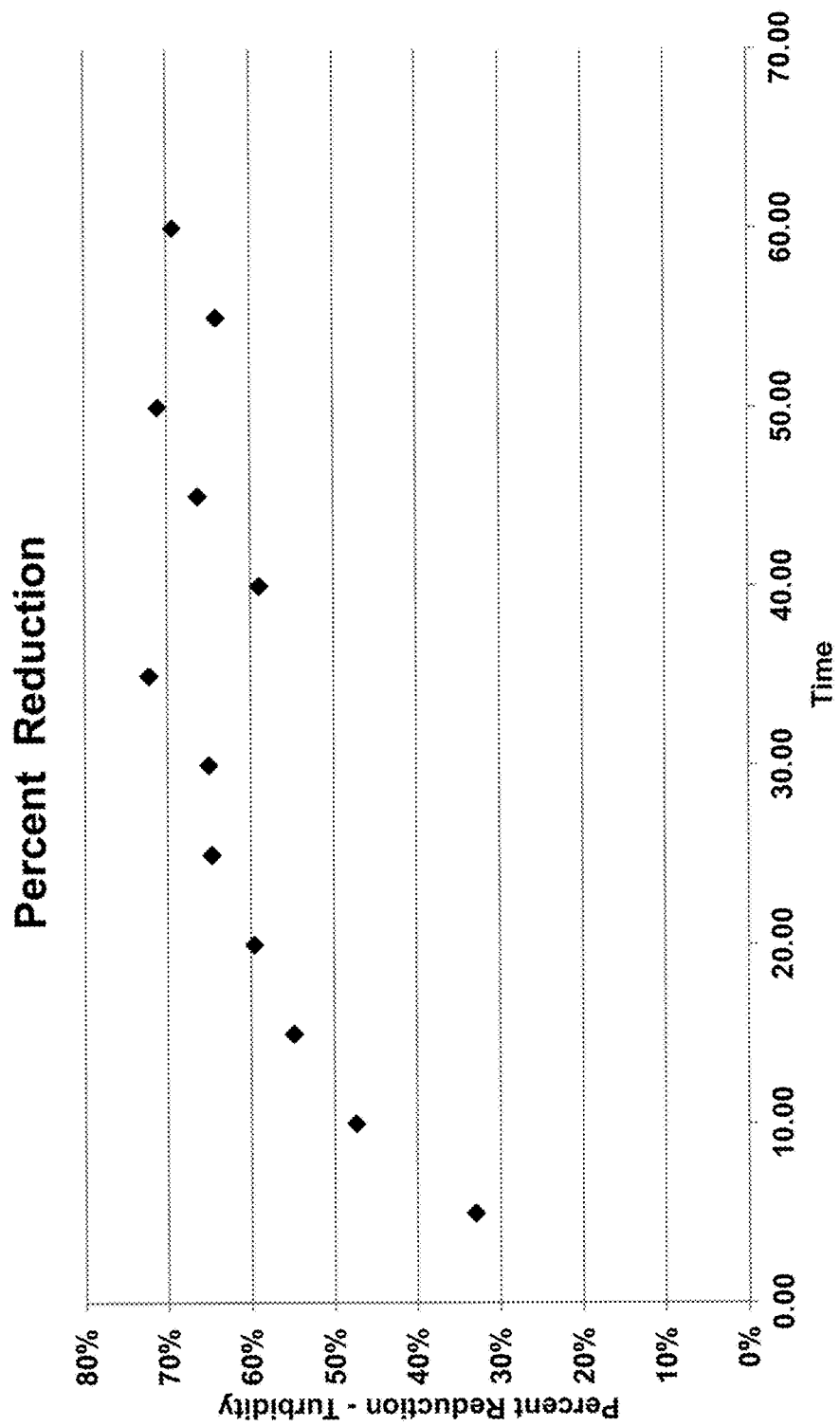
FIG. 7 is a graph showing the performance of an acoustophoretic device such as that illustrated in FIG. 1, at a frequency of 2.182 megahertz (MHz) and a flow rate of 30 mL/min. The graph has a y-axis of percent reduction, and runs from 0% to 80% in intervals of 10%. The x-axis is test duration in minutes, and runs from 0 to 70 in intervals of 10.
Figure 8:
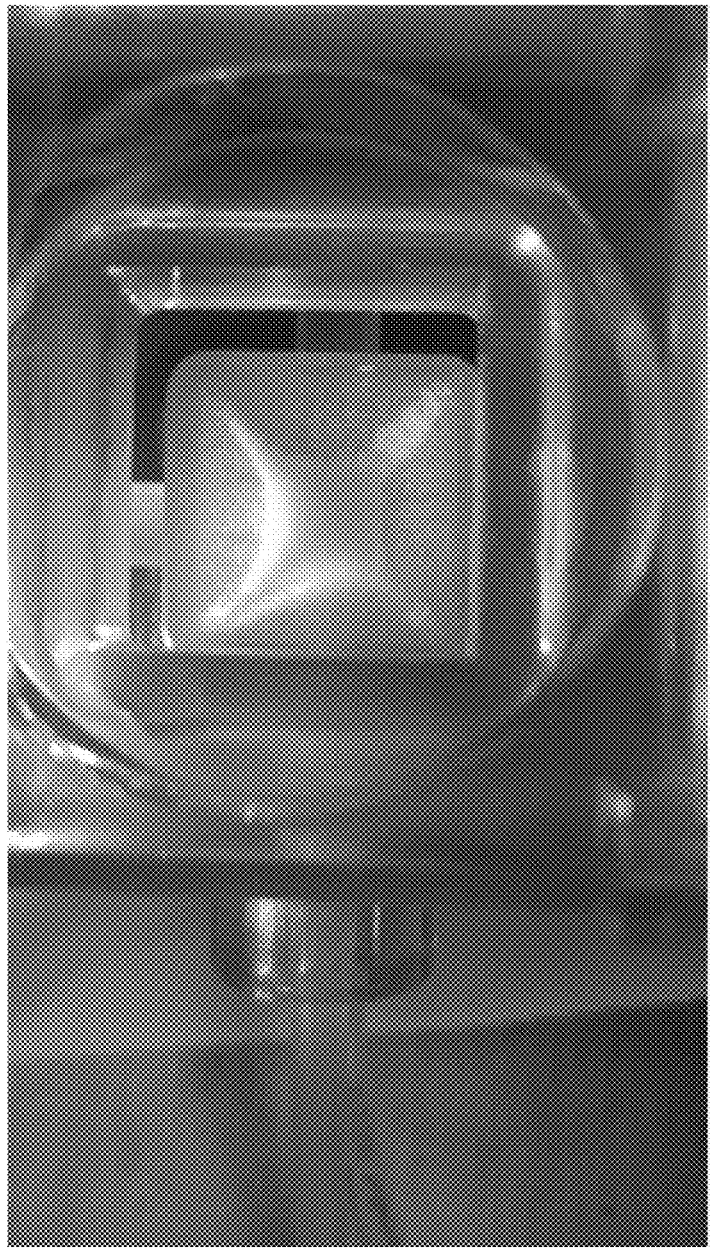
FIG. 8 is a photograph taken during the experiment of FIG. 7.

For the study depicted in FIG. 7, a mixture having a TCD of $1.52 \times 10^6$ cells/mL and TCC of $2.74 \times 10^9$ cells was used. In total, three tests were run with 1,800 mL of mixture flowed through the device at a flow rate of 30 mL/minute and the ultrasonic transducer operated at a starting frequency of 2.182 MHz. For each test, the turbidity was measured in NTU from the beginning of the test (time=0) to the end of the test (time=60 minutes) at intervals of five minutes. After testing, 1,800 mL of permeate was recovered and had a TCD of $4.30 \times 10^5$ cells/mL and a TCC of $7.74 \times 10^8$ cells. For the concentrate, 3 mL were recovered and had a TCD of $3.64 \times 10^8$ cells/mL and a TCC of $1.09 \times 10^9$ cells. FIG. 8 is a photograph of the yeast cells being concentrated in the flow chamber. When the three tests were averaged together, the device was shown to exhibit a volume concentration factor of 600, a cell retention rate of 40%, and a cell density reduction of 72%. The turbidity reduction performance of the device is summarized in the table below.

| Time | Test 1 NTU | Test 2 NTU | Test 3 NTU | Average | Reduction (%) |
|---|---|---|---|---|---|
| 0 | 20.5 | 19.94 | 20.5 | 20.31 | |
| 5 | 13.64 | 13.55 | 13.64 | 13.61 | 33 |
| 10 | 10.31 | 10.89 | 10.85 | 10.68 | 47 |
| 15 | 9.16 | 9.17 | 9.16 | 9.16 | 55 |
| 20 | 8.29 | 8.25 | 8.08 | 8.21 | 60 |
| 25 | 7.17 | 7.31 | 7.03 | 7.17 | 65 |
| 30 | 7.24 | 6.98 | 7.08 | 7.10 | 65 |
| 35 | 5.79 | 5.67 | 5.47 | 5.64 | 72 |
| 40 | 8.4 | 8.42 | 8.2 | 8.34 | 59 |
| 45 | 6.92 | 3.81 | 6.82 | 6.8 | 66 |
| 50 | 5.84 | 5.94 | 5.79 | 5.87 | 71 |
| 55 | 7.42 | 7.31 | 7.17 | 7.30 | 64 |
| 60 | 6.45 | 6.12 | 6.16 | 6.24 | 69 |

Figure 9:
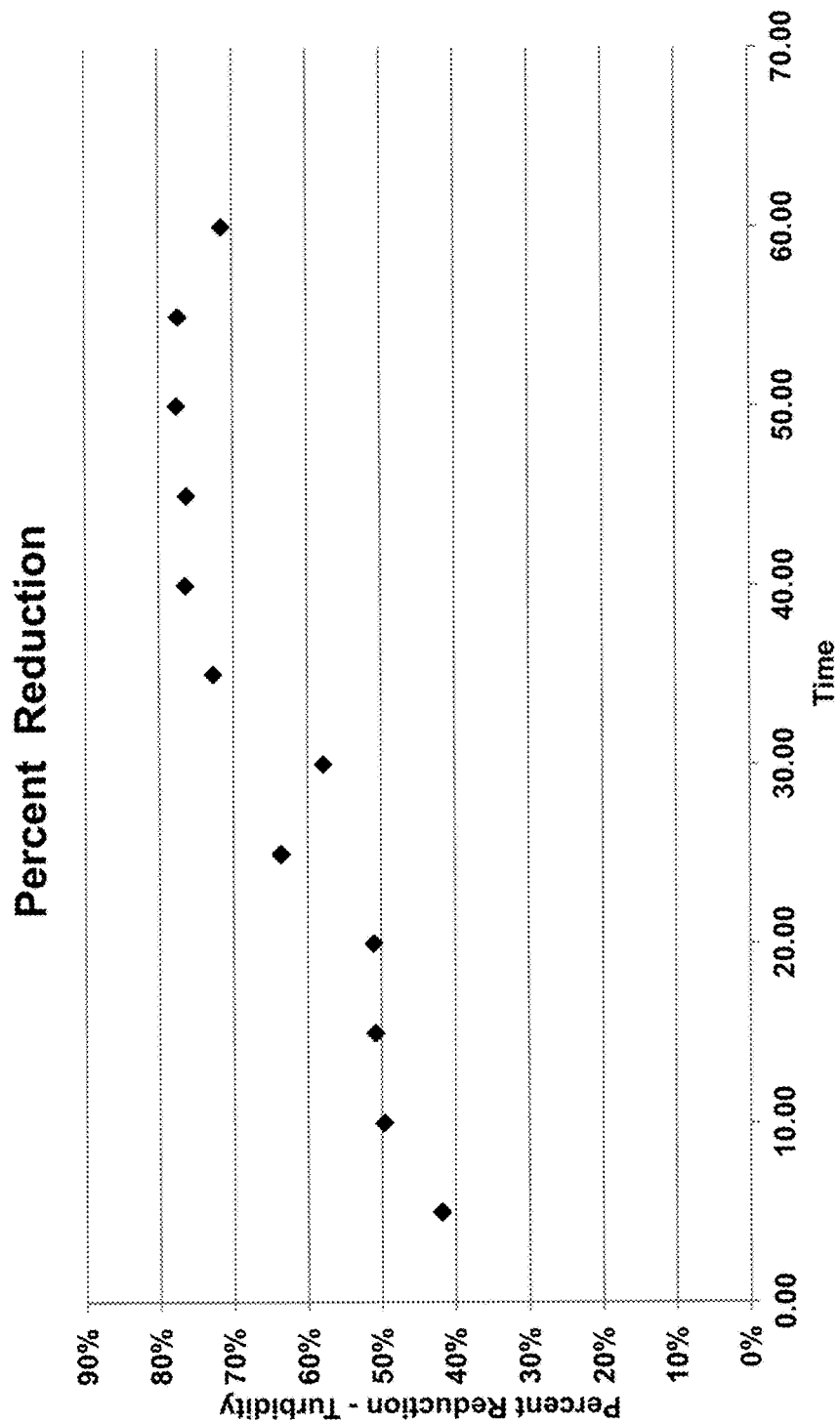
FIG. 9 is a graph showing the performance of an acoustophoretic device such as that illustrated in FIG. 1, at a frequency of 2.189 MHz and a flow rate of 30 mL/min. The graph has a y-axis of percent reduction, and runs from 0% to 90% in intervals of 10%. The x-axis is test duration in minutes, and runs from 0 to 70 in intervals of 10.

For the study depicted in FIG. 9, a mixture having a TCD of $1.52 \times 10^6$ cells/mL and TCC of $1.37 \times 10^9$ cells was used. In total, three tests were run with 900 mL of mixture flowed through the device at a flow rate of 30 mL/minute and the ultrasonic transducer operated at a starting frequency of 2.189 MHz. For each test, the turbidity was measured in NTU from the beginning of the test (time=0) to the end of the test (time=60 minutes) at intervals of five minutes. After testing, 900 mL of permeate were recovered and had a TCD of $5.10\times10^5$ cells/mL and a TCC of $4.59\times10^8$ cells. For the concentrate, 15 mL was recovered and had a TCD of $5.26\times10^7$ cells/mL and a TCC of $7.88\times10^8$ cells. When the three tests were averaged together, the device was shown to exhibit a volume concentration factor of 60, a cell retention rate of 58%, and a cell density reduction of 66%. The turbidity reduction performance of the device is summarized in the table below.

| Time | Test 1 NTU | Test 2 NTU | Test 3 NTU | Average | Reduction (%) |
|---|---|---|---|---|---|
| 0 | 21.8 | 21 | 20.1 | 20.97 | |
| 5 | 12.16 | 12.17 | 12.22 | 12.18 | 42 |
| 10 | 10.66 | 10.51 | 10.5 | 10.56 | 50 |
| 15 | 10.91 | 10.13 | 9.91 | 10.32 | 51 |
| 20 | 10.27 | 10.26 | 10.26 | 10.26 | 51 |
| 25 | 7.71 | 7.73 | 7.45 | 7.63 | 64 |
| 30 | 8.8 | 8.85 | 8.83 | 8.83 | 58 |
| 35 | 5.71 | 5.72 | 5.73 | 5.72 | 73 |
| 40 | 5.02 | 4.84 | 4.94 | 4.93 | 76 |
| 45 | 5.08 | 4.92 | 4.92 | 4.97 | 76 |
| 50 | 4.72 | 4.66 | 4.72 | 4.70 | 78 |
| 55 | 4.71 | 4.77 | 4.77 | 4.75 | 77 |
| 60 | 6.03 | 5.92 | 6 | 5.95 | 71 |

Figure 10:
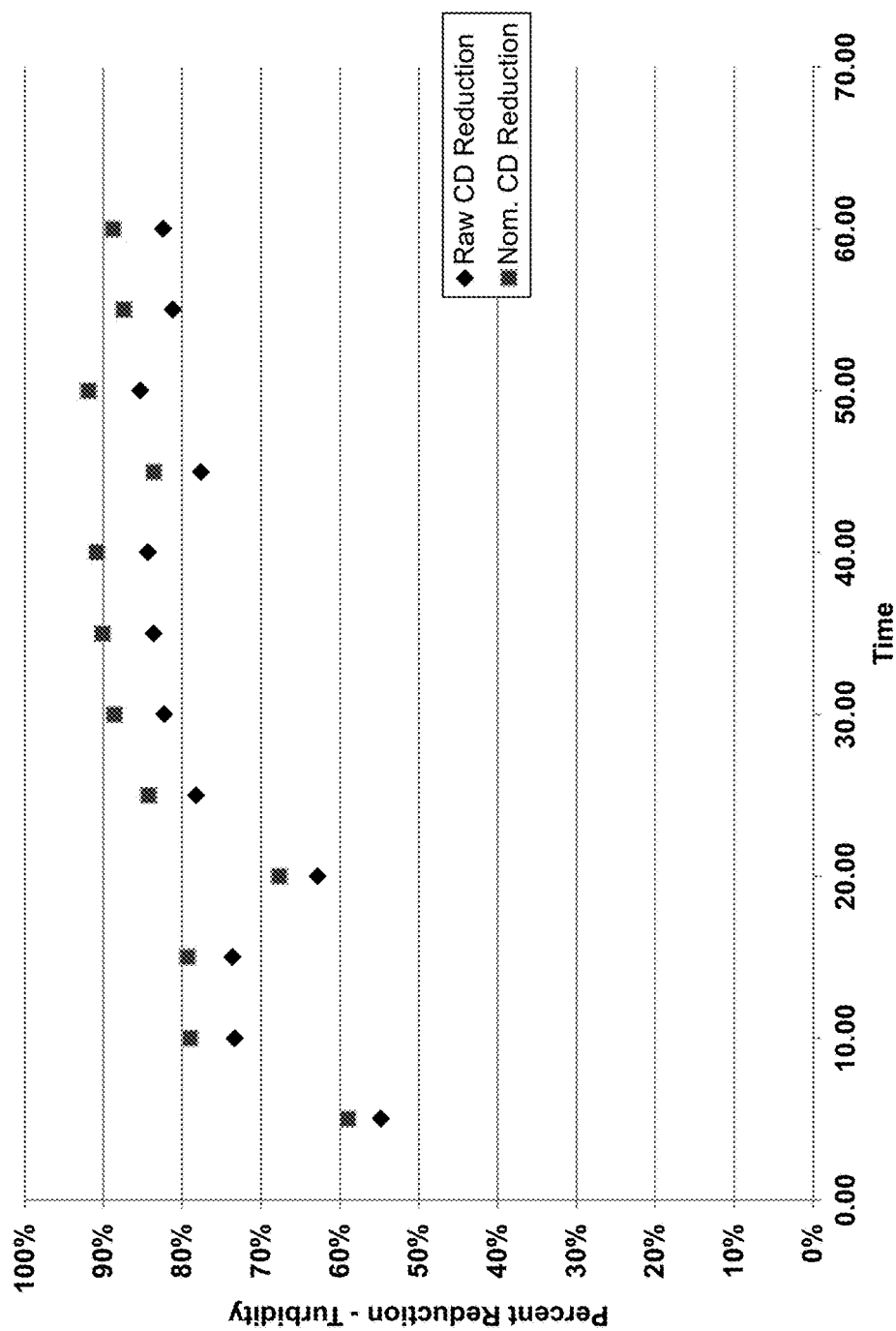
FIG. 10 is a graph showing the performance of an acoustophoretic device such as that illustrated in FIG. 1, at a frequency of 2.234 MHz and a flow rate of 15 mL/min. The graph has a y-axis of percent reduction, and runs from 0% to 100% in intervals of 10%. The x-axis is test duration in minutes, and runs from 0 to 70 in intervals of 10. The graph depicts data for raw cell density (CD) reduction in addition to nominalized cell density reduction.

For the study depicted in FIG. 10, a mixture having a TCD of $7.70\times10^5$ cells/mL and TCC of $6.93\times10^8$ cells was used. In total, three tests were run with 900 mL of mixture flowed through the device at a flow rate of 15 mL/minute and the ultrasonic transducer operated at a starting frequency of 2.234 MHz. For each test, the turbidity was measured in NTU from the beginning of the test (time=0) to the end of the test (time=60 minutes) at intervals of five minutes. After testing, 900 mL of permeate were recovered and had a TCD of $2.37\times10^5$ cells/mL and a TCC of $2.13\times10^8$ cells. For the concentrate, 3 mL were recovered and had a TCD of $2.28\times10^8$ cells/mL and a TCC of $6.84\times10^8$ cells. When the three tests were averaged together (both raw and nominalized), the device was shown to exhibit a volume concentration factor of 300, a cell retention rate of 99%, and a cell density reduction of 69%. The turbidity reduction performance of the device is summarized in the table below.

| | Test 1 NTU | Test 2 NTU | Test 3 NTU | Raw Avg | Nom Avg | Raw Reduc. | Nom Reduc. |
|---|---|---|---|---|---|---|---|
| Water Time | 1.48 | 1.54 | 1.44 | 1.49 | | | |
| 0 | 21.4 | 20.7 | 20.5 | 20.87 | 19.38 | | |
| 5 | 9.65 | 9.33 | 9.32 | 9.43 | 7.95 | 55% | 59% |
| 10 | 5.59 | 5.67 | 5.4 | 5.55 | 4.07 | 73% | 79% |
| 15 | 5.47 | 5.51 | 5.5 | 5.49 | 4.01 | 74% | 79% |
| 20 | 7.6 | 7.91 | 7.72 | 7.74 | 6.26 | 63% | 68% |
| 25 | 4.56 | 4.57 | 4.47 | 4.53 | 3.05 | 78% | 84% |
| 30 | 3.73 | 3.71 | 3.64 | 3.69 | 2.21 | 82% | 89% |
| 35 | 3.41 | 3.37 | 3.45 | 3.41 | 1.92 | 84% | 90% |
| 40 | 3.27 | 3.26 | 3.27 | 3.27 | 1.78 | 84% | 91% |
| 45 | 4.67 | 4.75 | 4.57 | 4.66 | 3.18 | 78% | 84% |
| 50 | 3.24 | 3.01 | 2.94 | 3.06 | 1.58 | 85% | 92% |
| 55 | 3.98 | 3.89 | 3.9 | 3.92 | 2.44 | 81% | 87% |
| 60 | 3.68 | 3.69 | 3.63 | 3.67 | 2.18 | 82% | 89% |

Figure 11:
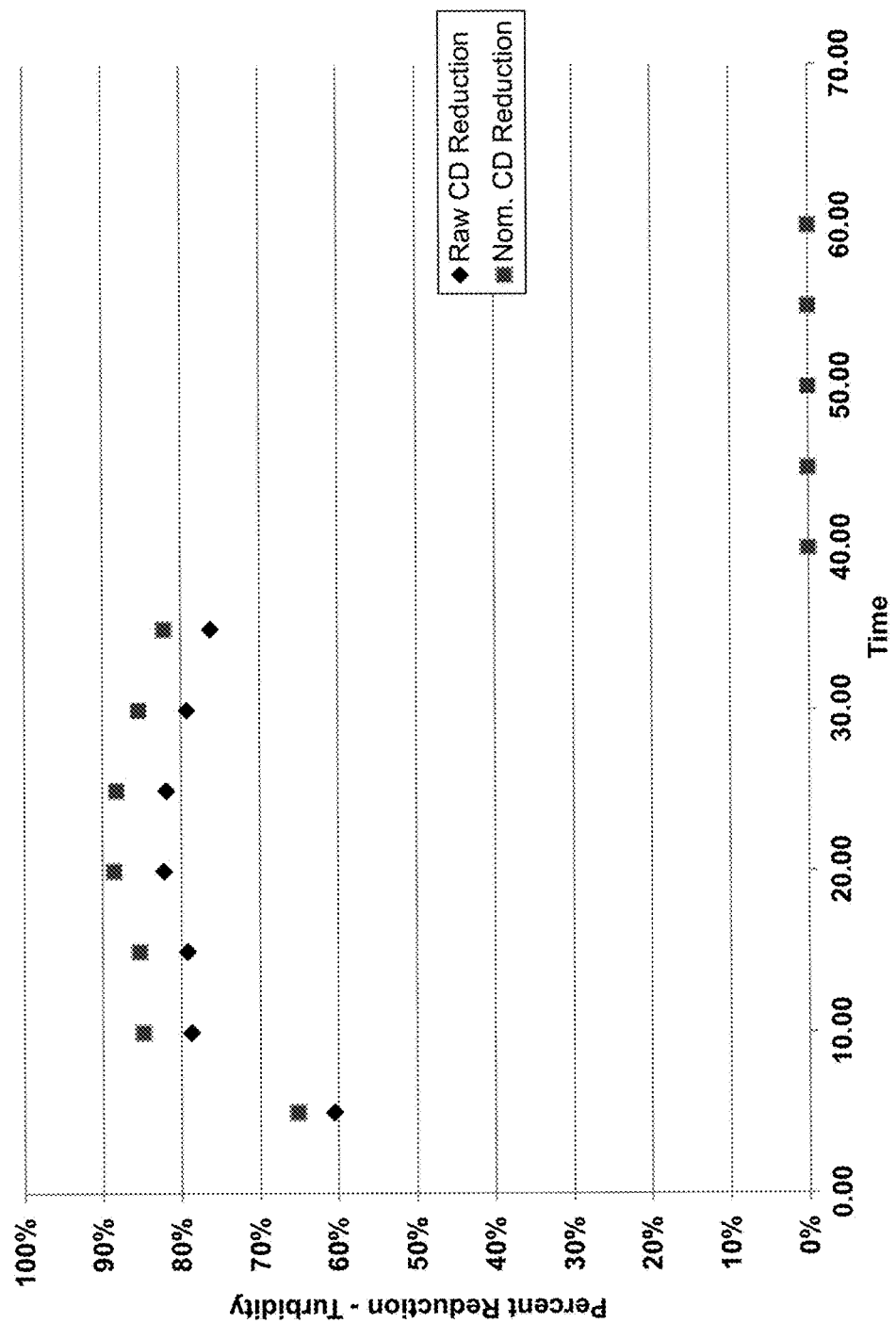
FIG. 11 is a graph showing the performance of an acoustophoretic device such as that illustrated in FIG. 1, at a frequency of 2.242 MHz and a flow rate of 15 mL/min. The graph has a y-axis of percent reduction, and runs from 0% to 100% in intervals of 10%. The x-axis is test duration in minutes, and runs from 0 to 70 in intervals of 10. The graph depicts data for raw cell density reduction in addition to nominalized cell density reduction.
Figure 12:
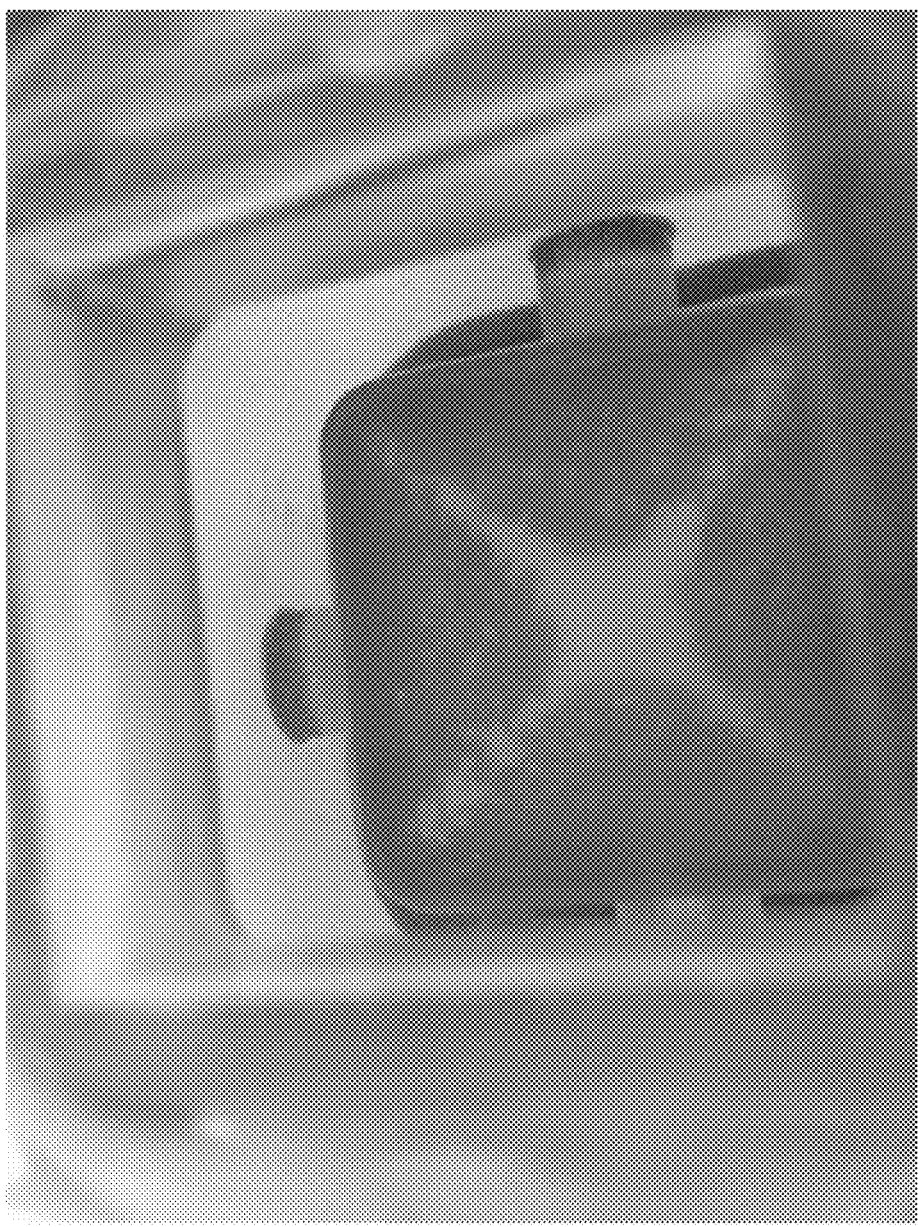
FIG. 12 is a photograph taken during the experiment of FIG. 11.

For the study depicted in FIG. 11, a mixture having a TCD of $7.70\times10^5$ cells/mL and TCC of $4.04\times10^8$ cells was used. In total, three tests were run with 525 mL of mixture flowed through the device at a flow rate of 15 mL/minute and the ultrasonic transducer operated at a starting frequency of 2.242 MHz. For each test, the turbidity was measured in NTU from the beginning of the test (time=0) to the end of the test (time=35 minutes) at intervals of five minutes. After testing, 525 mL of permeate were recovered and had a TCD of $4.07\times10^5$ cells/mL and a TCC of $2.14\times10^8$ cells. For the concentrate, 2 mL were recovered and had a TCD of $1.75\times10^8$ cells/mL and a TCC of $3.50\times10^8$ cells. FIG. 12 is a photograph of the yeast cells being concentrated in the flow chamber. When the three tests were averaged together (both raw and nominalized), the device was shown to exhibit a volume concentration factor of 262.5, a cell retention rate of 87%, a cell density reduction of 47%, and a cell concentration (CF) of 227.4 (i.e., the device concentrated the cells 227.4× their original concentration). The turbidity reduction performance of the device is summarized in the table below.

| | Test 1 NTU | Test 2 NTU | Test 3 NTU | Raw Avg | Nom Avg | Raw Reduc. | Nom Reduc. |
|---|---|---|---|---|---|---|---|
| Water Time | 1.48 | 1.54 | 1.44 | 1.49 | | | |
| 0 | 20.8 | 20.7 | 20.8 | 20.77 | 19.28 | | |
| 5 | 8.34 | 8.08 | 8.17 | 8.20 | 6.71 | 61% | 65% |
| 10 | 4.45 | 4.4 | 4.37 | 4.41 | 2.92 | 79% | 85% |
| 15 | 4.31 | 4.32 | 4.33 | 4.32 | 2.83 | 79% | 85% |
| 20 | 3.85 | 3.66 | 3.59 | 3.70 | 2.21 | 82% | 89% |
| 25 | 3.77 | 3.73 | 3.78 | 3.76 | 2.21 | 82% | 88% |
| 30 | 4.3 | 4.38 | 4.22 | 4.30 | 2.81 | 79% | 85% |
| 35 | 4.98 | 4.86 | 4.94 | 4.93 | 3.44 | 76% | 82% |

Figure 13:
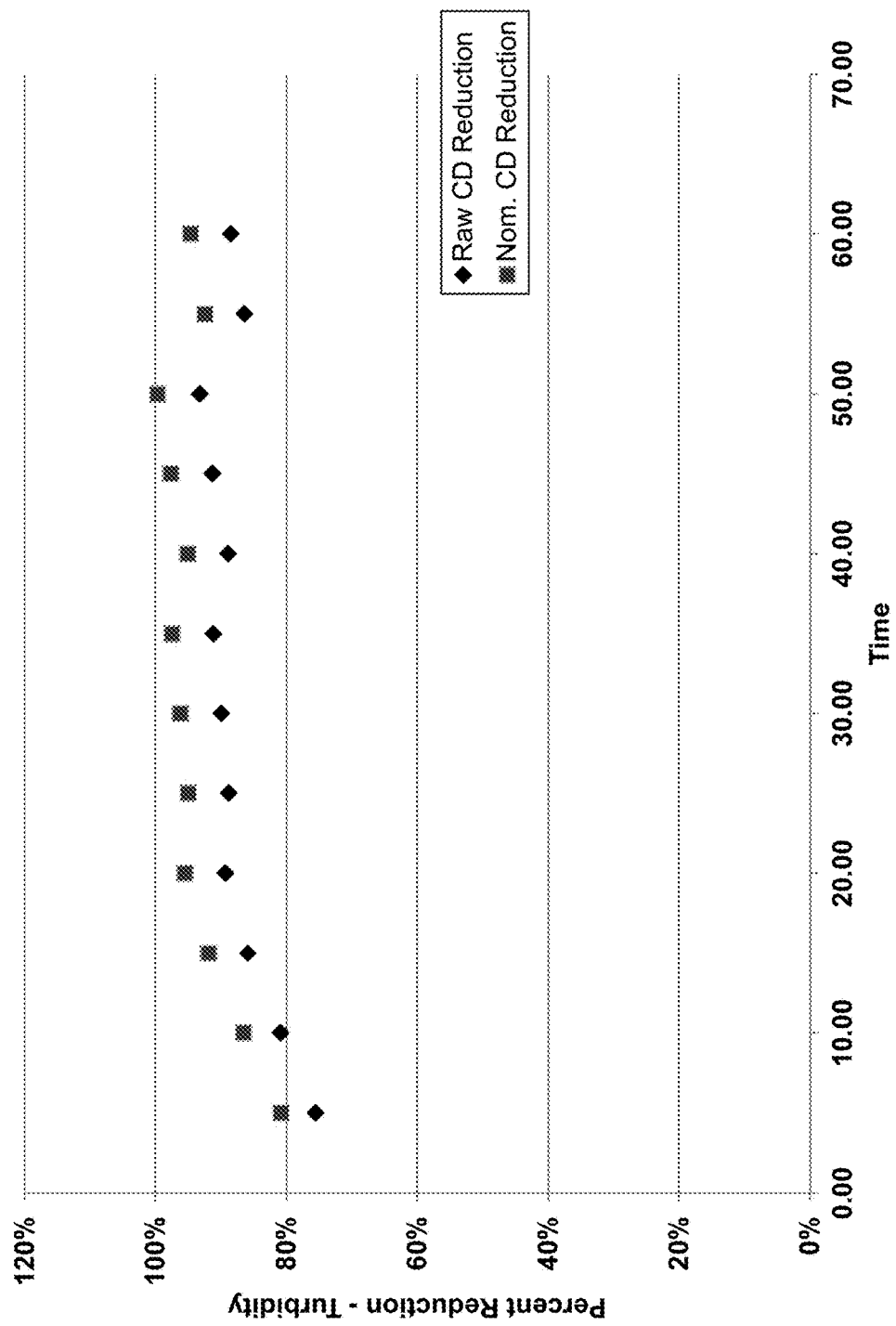
FIG. 13 is a graph showing the performance of an acoustophoretic device such as that illustrated in FIG. 1, at a frequency of 3.25 MHz and a flow rate of 15 mL/min. The graph has a y-axis of percent reduction, and runs from 0% to 120% in intervals of 20%. The x-axis is test duration in minutes, and runs from 0 to 70 in intervals of 10. The graph depicts data for raw cell density reduction and nominalized cell density reduction.
Figure 14:
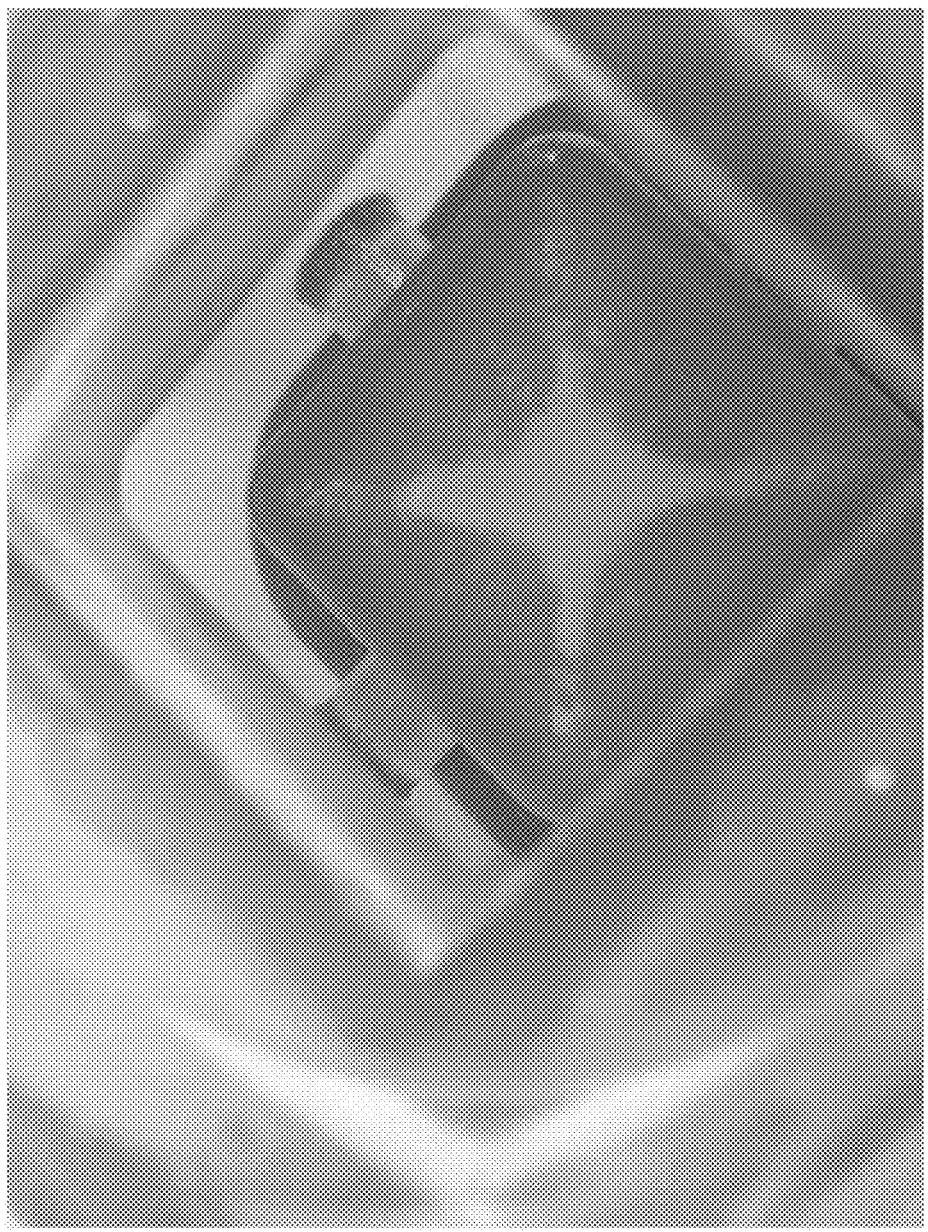
FIG. 14 is a photograph taken during the experiment of FIG. 13.

For the study depicted in FIG. 13, a mixture having a TCD of $7.70\times10^5$ cells/mL and TCC of $6.93\times10^8$ cells was used. In total, three tests were run with 900 mL of mixture flowed through the device at a flow rate of 15 mL/minute and the ultrasonic transducer operated at a starting frequency of 3.25 MHz. For each test, the turbidity was measured in NTU from the beginning of the test (time=0) to the end of the test (time=60 minutes) at intervals of five minutes. After testing, 900 mL of permeate were recovered and had a TCD of $1.53\times10^5$ cells/mL and a TCC of $1.38\times10^8$ cells. For the concentrate, 2.75 mL were recovered and had a TCD of $2.60\times10^8$ cells/mL and a TCC of $7.14\times10^8$ cells. FIG. 14 is a photograph of the yeast cells being concentrated in the flow chamber. When the three tests were averaged together (both raw and nominalized), the device was shown to exhibit a volume concentration factor of 327.3, a cell retention rate of 103%, a cell density reduction of 80%, and a cell concentration (CF) of 337.2 (i.e., the device concentrated the cells 337.2× their original concentration). The turbidity reduction performance of the device is summarized in the table below.

| | Test 1 NTU | Test 2 NTU | Test 3 NTU | Raw Avg | Nom Avg | Raw Reduc. | Nom Reduc. |
|---|---|---|---|---|---|---|---|
| Water Time | 1.48 | 1.54 | 1.44 | 1.49 | | | |
| 0 | 23 | 23 | 23 | 23.00 | 21.51 | | |
| 5 | 5.83 | 5.57 | 5.41 | 5.60 | 4.12 | 76% | 81% |
| 10 | 4.39 | 4.38 | 4.37 | 4.38 | 2.89 | 81% | 87% |
| 15 | 3.28 | 3.21 | 3.21 | 3.23 | 1.75 | 86% | 92% |
| 20 | 2.45 | 2.45 | 2.45 | 2.45 | 0.96 | 89% | 96% |
| 25 | 2.52 | 2.59 | 2.58 | 2.56 | 1.08 | 89% | 95% |
| 30 | 2.42 | 2.18 | 2.31 | 2.30 | 0.82 | 90% | 96% |
| 35 | 2.09 | 2.07 | 1.93 | 2.03 | 0.54 | 91% | 97% |

-continued

| | Test 1 NTU | Test 2 NTU | Test 3 NTU | Raw Avg | Nom Avg | Raw Reduc. | Nom Reduc. |
|---|---|---|---|---|---|---|---|
| 40 | 2.61 | 2.51 | 2.51 | 2.51 | 1.06 | 89% | 95% |
| 45 | 2.01 | 1.93 | 2.02 | 1.99 | 0.50 | 91% | 98% |
| 50 | 1.62 | 1.53 | 1.51 | 1.55 | 0.07 | 93% | 100% |
| 55 | 3.07 | 3.16 | 3.09 | 3.11 | 1.62 | 86% | 92% |
| 60 | 2.71 | 2.63 | 2.56 | 2.63 | 1.15 | 89% | 95% |

Figure 15:
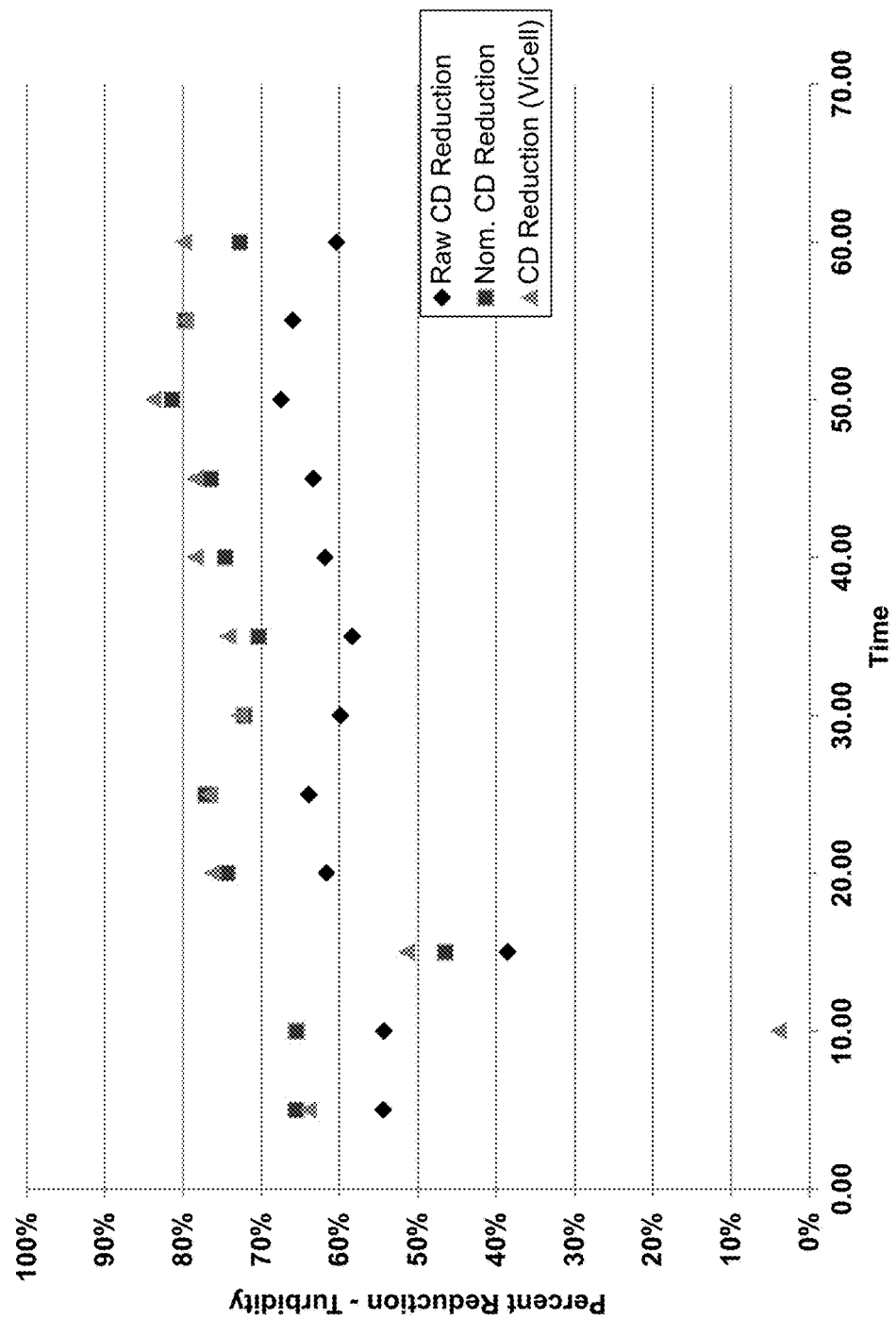
FIG. 15 is a graph showing the performance of an acoustophoretic device such as that illustrated in FIG. 1, at a frequency of 2.424 MHz and a flow rate of 15 mL/min. The graph has a y-axis of percent reduction, and runs from 0% to 120% in intervals of 20%. The x-axis is test duration in minutes, and runs from 0 to 70 in intervals of 10. The graph depicts data for raw cell density reduction, nominalized cell density reduction, and cell density reduction (VICell).
Figure 16:
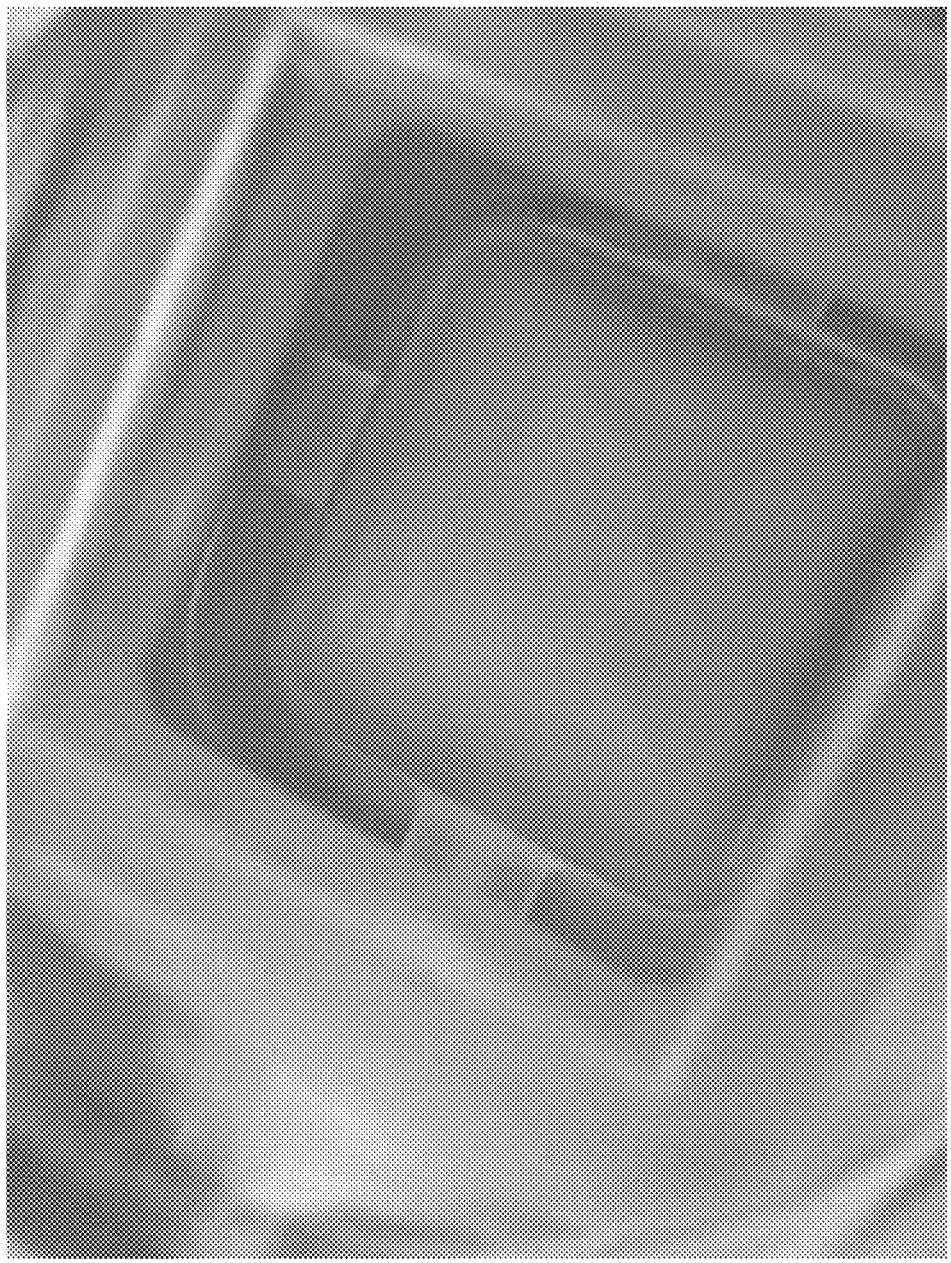
FIG. 16 is a photograph taken during the experiment of FIG. 15.

For the study depicted in FIG. 15, a mixture having a TCD of $1.23 \times 10^6$ cells/mL and TCC of $1.11 \times 10^9$ cells was used. In total, three tests were run with 900 mL of mixture flowed through the device at a flow rate of 15 mL/minute and the ultrasonic transducer operated at a starting frequency of 2.424 MHz. For each test, the turbidity was measured in NTU from the beginning of the test (time=0) to the end of the test (time=60 minutes) at intervals of five minutes. After testing, 900 mL of permeate were recovered and had a TCD of $2.50 \times 10^5$ cells/mL and a TCC of $2.25 \times 10^8$ cells. For the concentrate, 3 mL were recovered and had a TCD of $1.56 \times 10^8$ cells/mL and a TCC of $4.68 \times 10^8$ cells. FIG. 16 is a photograph of the yeast cells being concentrated in the flow chamber. When the three tests were averaged together (both raw and nominalized), the device was shown to exhibit a volume concentration factor of 300, a cell retention rate of 42%, a cell density reduction of 80%, and a cell concentration (CF) of 126.7 (i.e., the device concentrated the cells 126.7× their original concentration). The low cell retention rate for this test was caused by the collector overflowing during testing, causing many of the cells to be lost. The turbidity reduction performance of the device is summarized in the tables below, with SN signifying the supernatant.

| | Test 1 NTU | Test 2 NTU | Test 3 NTU | Raw Avg | Nom Avg | Raw Reduc. | Nom Reduc. |
|---|---|---|---|---|---|---|---|
| SN Time | 6.09 | 5.8 | 4.95 | 5.61 | | | |
| 0 | 32.5 | 33.1 | 33.1 | 32.90 | 27.29 | | |
| 5 | 14.9 | 14.99 | 15.09 | 14.99 | 9.38 | 54% | 66% |
| 10 | 15.05 | 14.97 | 15.02 | 15.01 | 9.40 | 54% | 66% |
| 15 | 20.02 | 20.3 | 20.3 | 20.21 | 14.59 | 39% | 47% |
| 20 | 12.59 | 12.5 | 12.71 | 12.60 | 6.99 | 62% | 74% |
| 25 | 11.9 | 11.84 | 11.79 | 11.84 | 6.23 | 64% | 77% |
| 30 | 13.25 | 13.13 | 13.18 | 13.19 | 7.57 | 60% | 72% |
| 35 | 13.75 | 13.71 | 13.6 | 13.69 | 8.07 | 58% | 70% |
| 40 | 12.59 | 12.44 | 12.55 | 12.53 | 6.91 | 62% | 75% |
| 45 | 11.93 | 11.82 | 12.34 | 12.03 | 6.42 | 63% | 76% |
| 50 | 11.03 | 10.52 | 10.5 | 10.68 | 5.07 | 68% | 81% |
| 55 | 11.5 | 11.07 | 10.9 | 11.16 | 5.54 | 66% | 80% |
| 60 | 13.09 | 12.98 | 13.03 | 13.03 | 7.42 | 60% | 73% |

| VICell | | |
|---|---|---|
| Time | Total Cells/mL (×10$^6$) | Reduction |
| 0 | 1.23 | |
| 5 | 0.44 | 64% |
| 10 | 1.18 | 4% |
| 15 | 0.60 | 51% |
| 20 | 0.29 | 76% |
| 25 | 0.29 | 77% |
| 30 | 0.33 | 73% |
| 35 | 0.32 | 74% |
| 40 | 0.26 | 78% |
| 45 | 0.26 | 78% |
| 50 | 0.20 | 84% |
| 55 | 0.25 | 80% |
| 60 | 0.25 | 80% |

Figure 17:
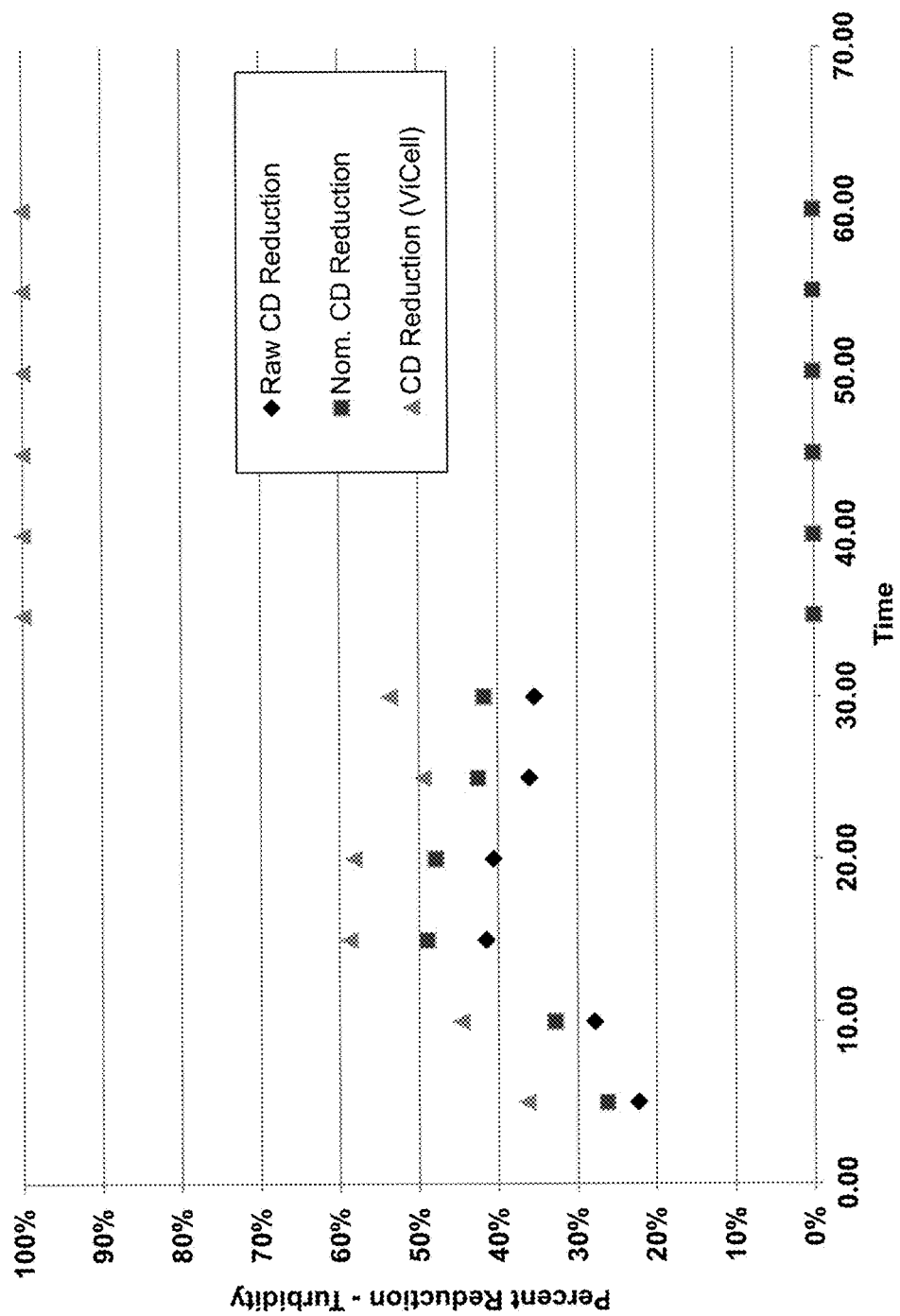
FIG. 17 is a graph showing the performance of an acoustophoretic device such as that illustrated in FIG. 1, at a frequency of 3.25 MHz and a flow rate of 15 mL/min. The graph has a y-axis of percent reduction, and runs from 0% to 100% in intervals of 10%. The x-axis is test duration in minutes, and runs from 0 to 70 in intervals of 10. The graph depicts data for raw cell density reduction, nominalized cell density reduction, and cell density reduction (VICell).
Figure 18:
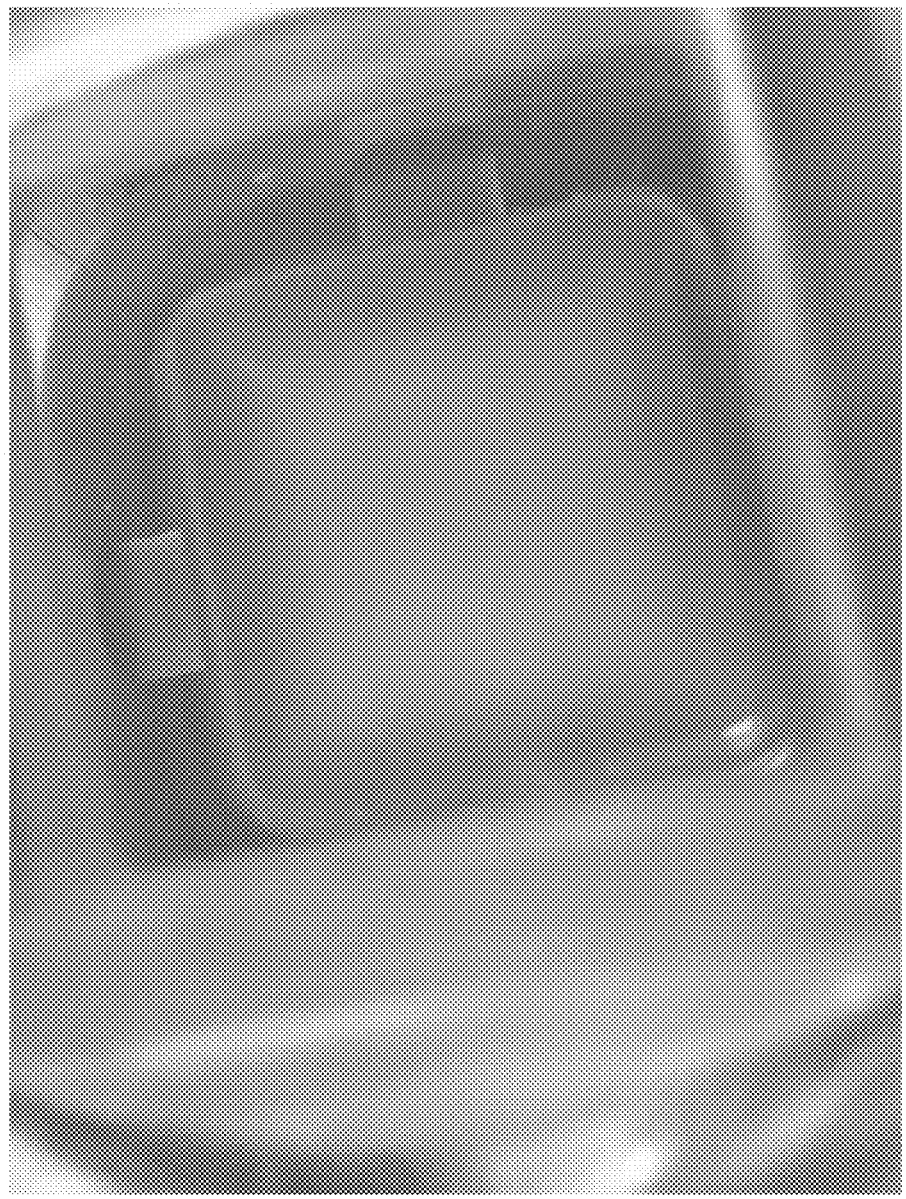
FIG. 18 is a photograph taken during the experiment of FIG. 17.

For the study depicted in FIG. 17, a mixture having a TCD of $1.44 \times 10^6$ cells/mL and TCC of $6.48 \times 10^8$ cells was used. In total, three tests were run with 450 mL of mixture flowed through the device at a flow rate of 15 mL/minute and the ultrasonic transducer operated at a starting frequency of 3.25 MHz. For each test, the turbidity was measured in NTU from the beginning of the test (time=0) to the end of the test (time=30 minutes) at intervals of five minutes. After testing, 450 mL of permeate were recovered and had a TCD of $6.70 \times 10^5$ cells/mL and a TCC of $3.02 \times 10^8$ cells. For the concentrate, 3 mL were recovered and had a TCD of $8.63 \times 10^7$ cells/mL and a TCC of $2.59 \times 10^8$ cells. FIG. 18 is a photograph of the yeast cells being concentrated in the flow chamber. When the three tests were averaged together (both raw and nominalized), the device was shown to exhibit a volume concentration factor of 150, a cell retention rate of 40%, a cell density reduction of 53%, and a cell concentration (CF) of 60 (i.e., the device concentrated the cells 60× their original concentration). The low cell retention rate for this test was caused by minimal cell loss from the collector during testing. The turbidity reduction performance of the device is summarized in the tables below, with SN signifying the supernatant.

| | Test 1 NTU | Test 2 NTU | Test 3 NTU | Raw Avg | Nom Avg | Raw Reduc. | Nom Reduc. |
|---|---|---|---|---|---|---|---|
| SN Time | 5.64 | 5.5 | 5.49 | 5.54 | | | |
| 0 | 36.7 | 36.5 | 36.4 | 36.53 | 30.99 | | |
| 5 | 28.3 | 28.4 | 28.5 | 28.40 | 22.86 | 22% | 26% |
| 10 | 26.4 | 26.4 | 26.3 | 26.37 | 20.82 | 28% | 33% |
| 15 | 21.3 | 21.4 | 21.4 | 21.37 | 15.82 | 42% | 49% |
| 20 | 21.8 | 21.7 | 21.6 | 21.70 | 16.16 | 41% | 48% |
| 25 | 23.6 | 23.2 | 23.3 | 23.37 | 17.82 | 36% | 42% |
| 30 | 23.7 | 23.6 | 23.5 | 23.60 | 18.06 | 35% | 42% |

| VICell | | |
|---|---|---|
| Time | Total Cells/mL (×10$^6$) | Reduction |
| 0 | 1.44 | |
| 5 | 0.91 | 36% |
| 10 | 0.80 | 45% |
| 15 | 0.59 | 59% |
| 20 | 0.60 | 58% |
| 25 | 0.73 | 49% |
| 30 | 0.67 | 54% |

Figure 19:
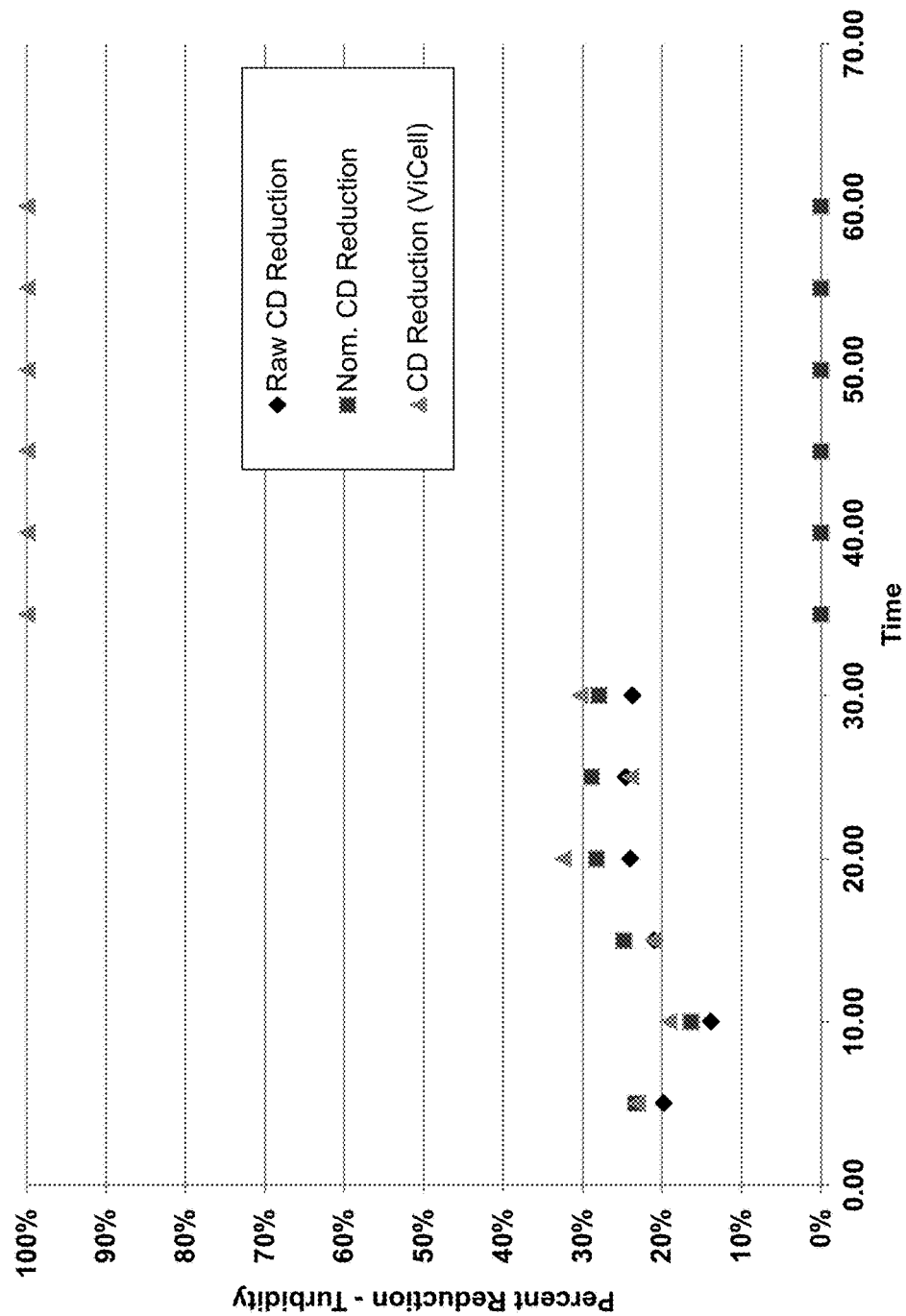
FIG. 19 is a graph showing the performance of an acoustophoretic device such as that illustrated in FIG. 1, at a frequency of 1.125 MHz and a flow rate of 15 mL/min. The graph has a y-axis of percent reduction, and runs from 0% to 100% in intervals of 10%. The x-axis is test duration in minutes, and runs from 0 to 70 in intervals of 10. The graph depicts data for raw cell density reduction, nominalized cell density reduction, and cell density reduction (VICell).

For the study depicted in FIG. 19, a mixture having a TCD of $1.11 \times 10^6$ cells/mL and TCC of $5.00 \times 10^8$ cells was used. In total, three tests were run with 450 mL of mixture flowed through the device at a flow rate of 15 mL/minute and the ultrasonic transducer operated at a starting frequency of 1.125 MHz. For each test, the turbidity was measured in NTU from the beginning of the test (time=0) to the end of the test (time=30 minutes) at intervals of five minutes. After testing, 450 mL of permeate were recovered and had a TCD of 8.34×10$^5$ cells/mL and a TCC of 3.75×10$^8$ cells. For the concentrate, 3 mL were recovered and had a TCD of 9.73×10$^7$ cells/mL and a TCC of 2.92×10$^8$ cells. When the three tests were averaged together (both raw and nominalized), the device was shown to exhibit a volume concentration factor of 150, a cell retention rate of 58%, a cell density reduction of 25%, and a cell concentration (CF) of 87.7 (i.e., the device concentrated the cells 87.7× their original concentration). The low cell retention rate for this test was caused by minimal cell loss from the collector during testing. The turbidity reduction performance of the device is summarized in the tables below, with SN signifying the supernatant.

|  | Test 1 NTU | Test 2 NTU | Test 3 NTU | Raw Avg | Nom Avg | Raw Reduc. | Nom Reduc. |
|---|---|---|---|---|---|---|---|
| SN | 5.64 | 5.5 | 5.49 | 5.54 |  |  |  |
| Time |  |  |  |  |  |  |  |
| 0 | 36.7 | 36.5 | 36.4 | 36.53 | 30.99 |  |  |
| 5 | 29.3 | 29.4 | 29.2 | 29.30 | 23.76 | 20% | 23% |
| 10 | 31.6 | 31.4 | 31.4 | 31.47 | 25.92 | 14% | 16% |
| 15 | 29.2 | 28.7 | 28.7 | 28.87 | 23.32 | 21% | 25% |
| 20 | 28.1 | 27.6 | 27.6 | 27.77 | 22.22 | 24% | 28% |
| 25 | 27.6 | 27.6 | 27.5 | 27.57 | 22.02 | 25% | 29% |
| 30 | 27.9 | 27.8 | 27.9 | 27.87 | 22.32 | 24% | 28% |

| VICell | | |
|---|---|---|
| Time | Total Cells/mL (×10$^6$) | Reduction |
| 0 | 1.11 |  |
| 5 | 0.86 | 23% |
| 10 | 0.90 | 19% |
| 15 | 0.88 | 21% |
| 20 | 0.75 | 33% |
| 25 | 0.85 | 24% |
| 30 | 0.77 | 30% |

The present disclosure has been described with reference to exemplary embodiments. Modifications and alterations may occur to others upon reading and understanding the preceding detailed description. It is intended that the present disclosure be construed as including all such modifications and alterations insofar as they come within the scope of the appended claims or the equivalents thereof.

The invention claimed is:

1. A method for concentrating target cells that include an original cell concentration in a host fluid, comprising:
   flowing a mixture of the host fluid and the target cells through an acoustophoretic device, the acoustophoretic device comprising:
      a flow chamber including at least one inlet and at least one outlet;
      at least one ultrasonic transducer coupled to the flow chamber, the at least one ultrasonic transducer including a piezoelectric material configured to be driven to create a multi-dimensional acoustic standing wave in the flow chamber; and
      a reflector on the opposite side of the flow chamber from the at least one ultrasonic transducer; and
   driving the at least one ultrasonic transducer to create the multi-dimensional acoustic standing wave in the flow chamber to concentrate the target cells;
   wherein the target cells are concentrated to a final concentration of at least 100 times the original cell concentration.

2. The method of claim 1, wherein the target cells are concentrated to a final concentration of about 150 times to about 300 times the original cell concentration.

3. The method of claim 1, wherein the target cells are concentrated to a final concentration of about 300 times to about 600 times the original cell concentration.

4. The method of claim 1, wherein the target cells include an original cell concentration of about 1 million cells per mL.

5. The method of claim 1, further comprising recovering the target cells in a final concentrated volume from the flow chamber.

6. The method of claim 5, wherein the total cell retention in the final concentrated volume is at least 80%.

7. The method of claim 1, wherein the acoustophoretic device is vertically oriented, such that the mixture flows vertically upwards from the at least one inlet toward the at least one outlet.

8. The method of claim 1, wherein the at least one inlet of the acoustophoretic device is located at a first end of the acoustophoretic device; and
   wherein the at least one outlet of the acoustophoretic device includes (i) a permeate outlet located at a second end of the device opposite the first end; and (ii) a concentrate outlet located between the at least one inlet and the at least one ultrasonic transducer, for recovering the target cells.

9. The method of claim 8, wherein the acoustophoretic device further comprises a collector located between the at least one inlet and the at least one ultrasonic transducer, the collector including at least one angled wall that tapers downwards in cross-sectional area, the collector being fluidly connected to the concentrate outlet.

10. The method of claim 9, wherein the mixture entering the device through the at least one inlet flow through an annular plenum around the collector.

11. The method of claim 9, wherein the concentrate outlet is located on a first side of the device.

12. The method of claim 9, wherein the multi-dimensional acoustic standing wave continuously traps the target cells, such that the target cells agglomerate, aggregate, clump, or coalesce together, and subsequently settle out of the host fluid and into the collector due to enhanced gravitational forces.

13. The method of claim 1, wherein the at least one inlet is located on a first side of the device such that the mixture turns prior to flowing through the flow chamber.

14. The method of claim 1, wherein the at least one ultrasonic transducer of the acoustophoretic device is a plurality of ultrasonic transducers arranged serially between the at least one inlet and the at least one outlet of the acoustophoretic device.

15. The method of claim 1, wherein the target cells are T cells, B cells, or NK cells.

16. The method of claim 1, wherein the turbidity of the host fluid is reduced by at least 65% after 60 minutes, or at least 70% after 60 minutes, or at least 80% after 60 minutes, or at least 90% after 60 minutes.

17. A method for obtaining concentrated target cells, comprising:
   flowing an original feed volume of a mixture of a host fluid and the target cells through an acoustophoretic device, the acoustophoretic device comprising:
      a flow chamber including at least one inlet and at least one outlet;
      at least one ultrasonic transducer coupled to the flow chamber, the at least one ultrasonic transducer including a piezoelectric material configured to be driven to create a multi-dimensional acoustic standing wave in the flow chamber; and a reflector opposite to the at least one ultrasonic transducer; and driving the at least one ultrasonic transducer to create the multi-dimensional acoustic standing wave, which continuously traps and concentrates the target cells; and recovering at least 40% the concentrated target cells in the original feed volume in a final concentrated volume, wherein the final concentrated volume is at least 100 times smaller than the original feed volume.

18. An acoustophoretic device for concentrating biological cells, comprising:

at least one inlet at a first end of the device;

a concentrate outlet on a first side of the device;

a flow chamber fluidly connected to the at least one inlet and the concentrate outlet;

at least one ultrasonic transducer coupled to the flow chamber, the at least one ultrasonic transducer including a piezoelectric material configured to be driven to create a multi-dimensional acoustic standing wave in the flow chamber; and a collector located between the at least one inlet and the at least one ultrasonic transducer, the collector including at least one angled wall that tapers downwards in cross-sectional area, the collector being fluidly connected to the concentrate outlet.

19. The device of claim 18, wherein the at least one inlet of the acoustophoretic device is located at a first end of the acoustophoretic device; and wherein the device further comprises a permeate outlet located at a second end of the device opposite the first end.

20. The device of claim 18, including an annular plenum around the collector fluidly connecting the at least one inlet to the flow chamber.

* * * * *